(12) United States Patent
Markey et al.

(10) Patent No.: US 8,366,719 B2
(45) Date of Patent: Feb. 5, 2013

(54) IMAGE-GUIDED MINIMAL-STEP PLACEMENT OF SCREW INTO BONE

(75) Inventors: Sean Markey, Castle Rock, CO (US); Chris Geiger, Castle Rock, CO (US)

(73) Assignee: Integrated Spinal Concepts, Inc., Parker, CO (US)

( * ) Notice: Subject to any disclaimer, the term of this patent is extended or adjusted under 35 U.S.C. 154(b) by 256 days.

(21) Appl. No.: 12/727,106

(22) Filed: Mar. 18, 2010

(65) Prior Publication Data

US 2010/0241129 A1    Sep. 23, 2010

Related U.S. Application Data

(60) Provisional application No. 61/161,332, filed on Mar. 18, 2009.

(51) Int. Cl.
*A61B 17/00* (2006.01)
*A61B 17/58* (2006.01)
*A61B 17/60* (2006.01)
*A61B 17/32* (2006.01)
*A61B 17/14* (2006.01)
*A61F 2/00* (2006.01)

(52) U.S. Cl. .......... 606/104; 606/80; 606/173; 606/180
(58) Field of Classification Search .......... 81/451; 606/104, 80, 173, 180
See application file for complete search history.

(56) References Cited

U.S. PATENT DOCUMENTS

| | | | | |
|---|---|---|---|---|
| 2,575,525 A * | 11/1951 | Mitchell | ......... | 81/431 |
| 4,243,388 A * | 1/1981 | Arai | ......... | 433/27 |
| 5,129,901 A | 7/1992 | Decoste | ......... | 606/65 |
| 5,925,048 A | 7/1999 | Ahmad et al. | ......... | 606/73 |
| 5,967,777 A | 10/1999 | Klein et al. | ......... | 433/75 |
| 6,096,042 A * | 8/2000 | Herbert | ......... | 606/80 |
| 6,106,464 A | 8/2000 | Bass et al. | ......... | 600/439 |
| 6,697,664 B2 | 2/2004 | Kienzle, III et al. | ......... | 600/427 |
| 6,776,069 B2 * | 8/2004 | Soreo et al. | ......... | 81/54 |
| 6,796,985 B2 * | 9/2004 | Bolger et al. | ......... | 606/80 |
| 6,917,827 B2 | 7/2005 | Kienzle, III | ......... | 600/427 |
| 6,980,849 B2 | 12/2005 | Sasso | ......... | 600/426 |
| 7,139,601 B2 | 11/2006 | Bucholz et al. | ......... | 600/407 |

(Continued)

FOREIGN PATENT DOCUMENTS

WO    WO2008027549    3/2008

OTHER PUBLICATIONS

Inspirstar Inc., "Product Sheet for Inspirstar ISO2BA Programmable Microcurrent Stimulator™," Printed from Internet on Mar. 18, 2010 at <URL: http://inspirstar.com/is02ba.php > 2 pages.

(Continued)

*Primary Examiner* — Kevin T Truong
*Assistant Examiner* — David Bates
(74) *Attorney, Agent, or Firm* — Merchant & Gould P.C.

(57) ABSTRACT

The present disclosure describes a device and methods for safely and accurately placing screws into bones with a powered driving device. By employing multiple layers of fail-safe features and image-guidance systems, the powered driving device provides safe, accurate, and efficient screw placement. That is, the powered driving device may continuously monitor a screw advancement and placement and may automatically shutdown when improper placement is detected. Monitoring placement may be conducted by a microcurrent-monitoring system, by an image-guidance system, or by any other appropriate sensory system. Additionally, upon detecting that screw insertion is complete, the powered driving device may be automatically shutdown. As screw placement is continuously simulated by image-guidance in real time, multiple redundant verification steps are eliminated, providing highly accurate screw placement while decreasing clinician error, device contamination, and surgical time, the decreased surgical time associated with decreased patient-recovery time and associated medical costs.

16 Claims, 13 Drawing Sheets

U.S. PATENT DOCUMENTS

| | | | |
|---|---|---|---|
| 7,887,548 B2* | 2/2011 | Usher et al. | 606/104 |
| 2002/0087101 A1 | 7/2002 | Barrick et al. | 600/587 |
| 2003/0093103 A1 | 5/2003 | Malackowski et al. | 606/170 |
| 2004/0044295 A1 | 3/2004 | Reinert et al. | 600/587 |
| 2004/0106916 A1 | 6/2004 | Quaid et al. | 606/1 |
| 2004/0167391 A1 | 8/2004 | Solar et al. | 600/411 |
| 2005/0101970 A1 | 5/2005 | Rosenberg | 606/130 |
| 2005/0137599 A1 | 6/2005 | Masini | 606/79 |
| 2005/0171553 A1* | 8/2005 | Schwarz et al. | 606/96 |
| 2005/0228270 A1 | 10/2005 | Lloyd et al. | 600/424 |
| 2005/0267354 A1 | 12/2005 | Marquart et al. | 600/411 |
| 2006/0009780 A1 | 1/2006 | Foley et al. | 606/99 |
| 2006/0058616 A1 | 3/2006 | Marquart et al. | 600/407 |
| 2006/0079903 A1 | 4/2006 | Wong | 606/72 |
| 2006/0241628 A1* | 10/2006 | Parak | 606/80 |
| 2007/0016009 A1 | 1/2007 | Lakin et al. | 600/424 |
| 2008/0013678 A1 | 1/2008 | Magerl et al. | 378/20 |
| 2008/0125637 A1* | 5/2008 | Geist et al. | 600/372 |
| 2008/0161680 A1 | 7/2008 | Von Jako et al. | 600/424 |
| 2008/0228188 A1 | 9/2008 | Birkbeck et al. | 606/87 |
| 2008/0255584 A1 | 10/2008 | Beverland et al. | 606/130 |
| 2009/0054910 A1 | 2/2009 | Zheng et al. | 606/130 |

OTHER PUBLICATIONS

NuVasive, "Creative Spine Technolgy®, Surgeon Resources," Printed from Internet on Mar. 18, 2010 at <URL: http://www.nuvasive.com/surgeons/lumbar.htm > 3 pages.

Spine Universe, "Image-Guided Surgery: Space Age Technology Enters the Operating Room," Printed from Internet on Jun. 18, 2010 at <URL: http://www.spineuniverse.com/exams-tests/devices/image-guided-surgery-space-age-technology-enters > 3 pages.

Spine Universe, "Advancements in Spine Surgery," Printed from Internet on Jun. 18, 2010 at < URL: http://www.spineuniverse.com/exams-tests/devices/advancements-spine-surgery > 2 pages.

POWEREASE™ Surgial Instrument System for Medtronic "A next-generation system of medical tools for spine syrgery," Project date 2012, retrieved from URL: http://www.ideo.com/work/powerease-surgical-instrument-system (Nov. 2, 2012 9:16:25 AM).

Medtronic New Release "Medtronic Announces Launch of the POWEREASE™ System," Apr. 16, 2012, retrieved form URL: http://wwwp.medtronic.com/Newsroom/NewsReleaseDetails.do?itemId=1334574786493 (Nov. 2, 2012 9:26:14 AM).

* cited by examiner

IMAGE-GUIDED MINIMAL-STEP PLACEMENT OF SCREW INTO BONE

CROSS-REFERENCE TO RELATED APPLICATIONS

This application claims the benefit of U.S. Provisional Application Ser. No. 61/161,332, filed Mar. 18, 2009, the complete disclosure of which is hereby incorporated by reference in its entirety.

INTRODUCTION

Surgical procedures involving the bones of the spine are among the most dangerous, lengthy, and costly surgeries presently performed. A primary reason that these surgeries are so dangerous is due to the proximity of the spinal bones to the spinal cord. Thus, even slight miscalculations and inaccuracies during a spinal procedure may have devastating results, including patient paralysis or death. Consequently, spinal surgeries involve meticulous care and multiple safeguards and precautions—resulting in extremely time-consuming procedures. Although precision and accuracy are paramount, lengthy procedures are associated with additional risks and dangers. In fact, studies have found a direct relationship between surgical time and patient recovery time, i.e., patient recovery time increases as surgical time increases. In addition, surgical time is directly linked to the likelihood of infection, i.e., the longer a surgical procedure, the more likely a patient is to suffer from a secondary infection. Finally, the length of a surgical procedure is directly linked to the cost of that surgical procedure. Thus, increasing the speed, accuracy, and efficiency of delicate medical procedures, such as spinal surgery, may improve patient recovery and profoundly reduce presently-soaring healthcare costs.

As described above, current spinal procedures, including neurosurgical, orthopedic, etc., involve meticulous care in combination with numerous manual steps and safeguards. For example, image guidance may be employed to repeatedly verify numerous manual screw insertion steps. That is, a guide hole for a screw may be drilled (without image-guidance) and then verified, the guide hole may be tapped with an awl (manually) and then verified, the tapped guide hole may be re-tapped to reposition the trajectory (manually) and then verified, the screw may be rotated into the verified tapped guide hole (manually) and then verified, the screw may be removed (manually) and the screw channel may be again verified before final insertion.

As may be appreciated, current spinal surgeries are primarily manual with highly redundant verification steps. This redundancy, while potentially increasing precision on the one hand, may increase the opportunity for clinician error, device malfunction, and device contamination on the other. In addition, as noted above, because surgical time is greatly increased by this multi-step procedure, patient recovery time, risk of infection, and associated medical costs are also correspondingly increased. Indeed, associated medical costs may be compounded by both increased surgical time and staffing in hospital facilities and by increased hospital stays due to the increased patient recovery time and complications brought on by secondary infections. Further, as the present procedures are dependent on manual rotation for placement of the screw, inaccurate screw placement in patients with diseased bone or uncharacteristic anatomical landmarks may also be increased, along with a high probability of multiple X-rays to confirm accurate screw placement.

As such, there is a need for a highly accurate and efficient procedure for inserting a screw into a bone during a spinal-fixation procedure.

Image-Guided Minimal-Step Placement of Screw into Bone

The present disclosure describes devices and methods for placing screws into bones. Specifically, the disclosed devices allow for powered insertion of screws into bones with an unprecedented degree of accuracy, precision and safety. Indeed, the present methods directly address and meet any potential concerns regarding use of a powered driving device in close proximity to delicate areas of the body, e.g., the spinal cord and nerves, while also eliminating many of the limitations and detriments of current procedures. That is, by employing multiple layers of fail-safe features, the powered driving devices arguably exceed present multi-step procedures in safety. Further, by integrating the powered driving devices with image-guidance systems, precision of screw placement is automatically provided without repeated verification of a planned trajectory associated with manual insertion. Indeed, by eliminating many of the redundant verification steps, the methods provide a decreased opportunity for clinician error, decreased opportunity for device contamination, and decreased surgical time with associated decreased patient-recovery time and decreased associated medical costs. In fact, the present methods are estimated to reduce surgical time by up to half, revolutionizing present spinal-fixation procedures and profoundly impacting a myriad of other delicate surgical procedures.

Embodiments disclosed herein provide methods for inserting a screw into bone using a powered driving device. For example, according to embodiments, the powered driving device may be registered in an image-guided field. Further, the methods may comprise identifying a target position for delivering the screw into the bone, where the target position is associated with a target insertion location at a target trajectory, and receiving an indication from the powered driving device when the powered driving device is positioned over the target insertion location and is oriented according to the target trajectory. Thereafter, the methods may include docking the powered driving device over the target insertion location and initiating the powered driving device to advance the screw into the bone. During advancement of the screw into the bone, a position of the screw may be monitored by the powered driving device. The screw may then be delivered into the target position.

According to additional embodiments, a powered driving device for minimal-step placement of a screw into bone is provided. The powered driving device may comprise a drive component configured for delivering torque to a drive shaft, which is communicatively coupled to the drive component. The drive shaft may be configured to rotate axially when torque is delivered by the drive component. Further, the powered driving device may comprise a drive chamber that encases the drive component and the drive shaft and houses a screw. When housed in the drive chamber, the screw may couple to the drive shaft. The powered driving device may also comprise a monitoring component for detecting a position of the screw and an alert component for issuing an alert when the monitoring component detects that the screw has an improper trajectory. In addition, the powered driving device may comprise a safety trigger for automatically shutting down the powered driving device when the monitoring component detects the screw is in an improper position.

According to additional embodiments, a method for automatically shutting down a powered driving device while inserting a screw into bone may be provided. The method may comprise monitoring advancement of the screw in real time during powered delivery of the screw into the bone and automatically shutting down the powered driving device upon detecting that the specialized screw is in an improper position.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structures particularly pointed out in the written description and claims herein as well as the appended drawings.

It is to be understood that both the foregoing general description and the following detailed description are exemplary and explanatory and are intended to provide further explanation of the embodiments as claimed.

BRIEF DESCRIPTION OF THE DRAWINGS

The following drawing figures, which form a part of this application, are illustrative of the described technology and are not meant to limit the scope of the embodiments as claimed in any manner, which scope shall be based on the claims appended hereto.

DETAILED DESCRIPTION

Before the present methods and powered driving devices for image-guided, minimal-step placement of screws into bone are disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

The present disclosure describes devices and methods for placing screws into bones with a powered driving device. By employing multiple layers of fail-safe features and image-guidance systems, the powered driving devices provide safe, accurate, and efficient screw placement. That is, the powered driving devices may continuously monitor a screw advancement and placement and may automatically and substantially immediately shutdown when inaccurate advancement or placement is detected. Monitoring placement may be conducted by an electrical current monitoring system (e.g., a micro-current monitoring system), by an image-guidance system, or by any other appropriate system. Additionally, upon detecting that insertion is complete, the powered driving device may be automatically and substantially immediately shutdown. As screw placement is continuously simulated by image-guidance in real time, multiple redundant verification steps are eliminated, providing highly accurate screw placement while decreasing clinician error, device contamination, and surgical time, the decreased surgical time further associated with decreased patient-recovery time and associated medical costs.

Although the techniques introduced above and discussed in detail below may be implemented for a variety of medical procedures, the present disclosure will discuss the implementation of these techniques for use in a power-driven, image-guided, minimal-step placement of a pedicle screw into a pedicle. The reader will understand that the technology described in the context of placing pedicle screws into pedicles could be adapted for use with other precision systems in which power-driven, image-guided placement of implants or screws is implicated, e.g., plates, screws, and other implants for insertion into cranial bones, bones of the extremities, etc.

Figure 1:
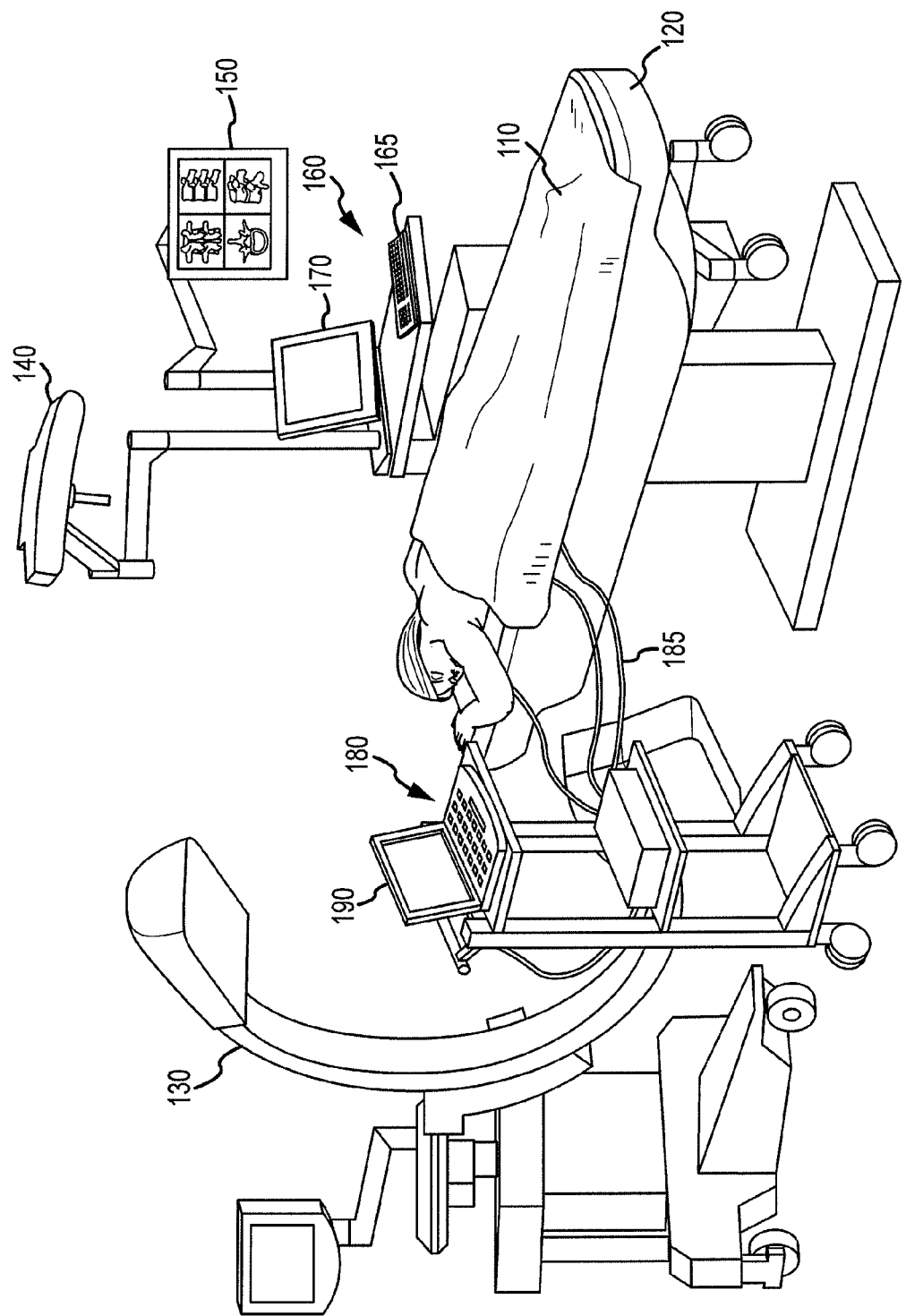
FIG. 1 is an illustration of embodiments of surgical devices and systems for performing a surgical procedure.

FIG. 1 is an illustration of embodiments of surgical devices and systems for performing a surgical procedure.

The following general discussion relates to various surgical devices and systems available to a clinician during a surgical procedure, e.g., a spinal-fixation procedure, in an exemplary operating room (OR). According to embodiments related to the spinal-fixation procedure, a patient 110 may be placed in a prone position over a frame (not shown) or table 120 that allows the patient's abdominal region to hang free, preventing intra-abdominal pressure that may increase intra-operative bleeding.

The OR may further provide an image-guidance system, or image-guided navigation system, including various displays and monitors, one or more computing systems, various X-ray and other imaging devices, etc. For example, a surgical image-guidance system may be provided that maps positions of surgical tools and implants onto images of a patient's anatomy. Both two- and three-dimensional images, sometimes referred to as "image sets," may be employed by image-guidance systems, including preoperative images (i.e., images generated prior to a surgical procedure) and intra-operative images (i.e., image sets generated during the surgical procedure). Two-dimensional image sets may commonly include fluoroscopic images and may be generated intra-operatively using a C-arm fluoroscope, e.g., C-arm fluoroscope 130. Three-dimensional image sets, generally obtained preoperatively, may include one or more of the following: magnetic resonance imaging (MRI) scans, computer tomography (CT) scans, positron emission tomography (PET) scans, and angiographic data. Indeed, any two- or three-dimensional imaging now known or developed in the future may be employed in an image-guidance system within the spirit of the present disclosure.

According to an embodiment, for example, volumetric data from the patient 110 may be collected by the C-arm fluoroscope 130, an intra-operative CT scanning device (not shown), or other suitable imaging device, such that a plurality of images may be obtained while the device rotates roughly 190 degrees about the patient 110. The volumetric data may then be loaded into the image-guidance system and converted into a plurality of image sets that may be rendered on image display 150, for example. As illustrated, image display 150 may provide a plurality of image views, e.g., transverse, caudal, sagittal, axial, etc., and may provide a plurality of image types, e.g., two- and three-dimensional image types.

According to some embodiments, a clinician may develop a preoperative surgical plan by determining a target position of an implant and, based on the target position, calculating a target insertion location and a target trajectory for properly guiding the pedicle screw into the target position. The surgeon may also determine an estimated size and/or type of screw, which may later be verified by intra-operative imaging procedures.

Figure 7A:
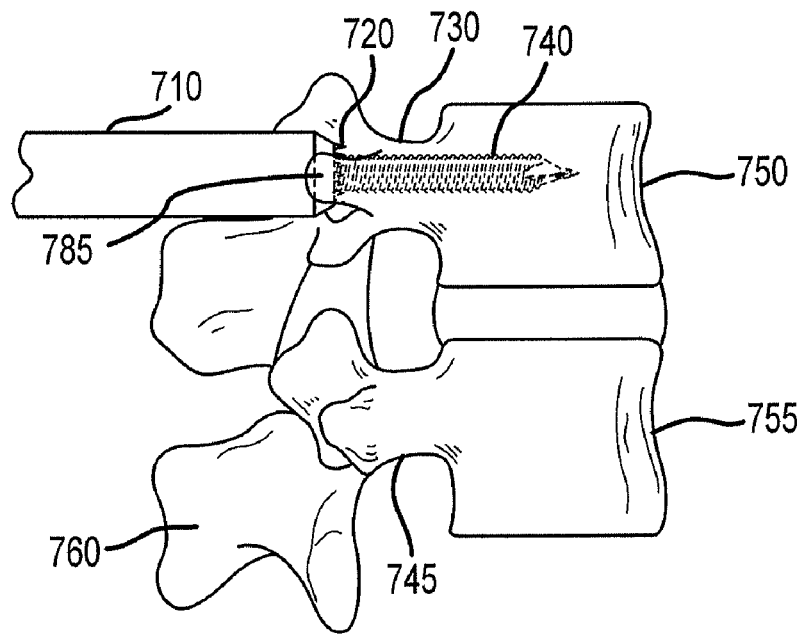
FIG. 7A is an illustration of a sagittal view of an embodiment of a properly placed screw in a pedicle as described herein.
Figure 7B:
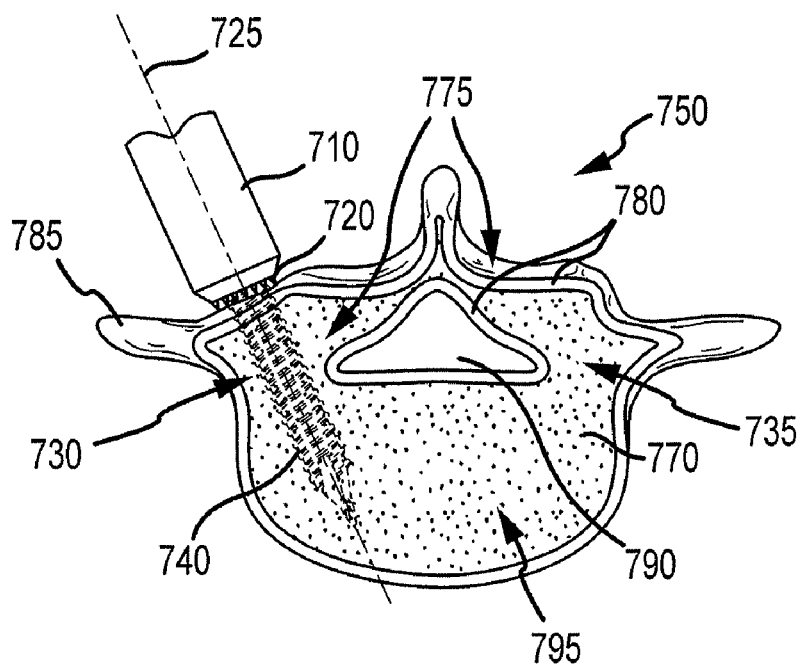
FIG. 7B is an illustration of an axial view of an embodiment of a properly placed screw in a pedicle as described herein.

According to embodiments, an image-guidance field may be established by affixing a stationary tracker to a spinous process of the patient's backbone (see FIGS. 7A and 7B for an illustration of a spinous process). The stationary tracker may comprise a plurality of light-emitting diodes (LEDs) that emit pulses, or bursts, of infrared radiation detectable by a stereo camera apparatus 140. For example, stereo camera apparatus 140 may be affixed in any suitable location and focused around an area of interest, e.g., above surgical table 120, and may be sensitive to infrared radiation. According to alternative embodiments, the stationary tracker may comprise a plurality of mirror-like balls that passively reflect incident infrared radiation (e.g., emitted by an infrared radiation source) and that are detectable by stereo camera apparatus 140. According to other embodiments, a magnetic image-guidance system may utilize a field generator for producing a magnetic field and the stationary tracker may comprise a plurality of small coils. According to still other embodiments, a global positioning system (GPS) may be employed. Data regarding the location of the stationary tracker within three-dimensional space may be collected by the stereo camera apparatus 140, electromagnetic detector, or GPS system, and may be fed into the image-guidance system.

Thereafter, according to embodiments, the image-guidance field may be verified using fiducial markers, i.e., markers used as reference points to establish XYZ coordinates within the three-dimensional space of the image-guidance field. Fiducial markers, generally but not limited to four, may refer to a random array of anatomical landmarks of known location within a patient's body. An image-guided probe, or other suitable device, may be used to register the fiducial markers to the displayed images. According to embodiments, the location of the image-guided probe may be represented on the display images, e.g., via any suitable visual indication or icon. The image-guidance system may be verified by touching the image-guided probe to each of the fiducial markers to verify that the visual indication of the image-guided probe corresponds to the anatomical landmark recognizable by the clinician on the images. Specifically, the location of the image-guided probe may correspond to the location of the anatomical landmark to within an acceptable degree of deviance, e.g., 1 millimeter (mm). In the case of an unacceptable degree of image deviance, a point-to-point registration may be used to recollect imaging data. Once accuracy of the image-guidance field is established, the image-guided probe may be touched to other known anatomical features and landmarks within a surgical site, again confirming accuracy of the image-guidance system.

According to embodiments, one or more surgical tools may also be registered, or calibrated, to the verified image-guidance system. For example, each surgical tool may be fitted with light-emitting diodes or global positioning systems and data regarding the position of the surgical tool may be collected by the stereo camera apparatus 140, a GPS system, or otherwise. Registration or calibration may refer to the process of mapping a tracked position of an actual element within three-dimensional space (e.g., device, implant, anatomical landmark, etc.) to a virtual position of that element on image displays. Thus, calibration enables the image-guidance system to continuously track a position of the one or more surgical tools, or instruments, within the display images in real-time. That is, with knowledge of the relationship between a position of a surgical tool and the patient's anatomy and the relationship between the patient's anatomy and the images, the image-guidance system is able to continually superimpose a representation of the tool on the displayed images that corresponds to the relationship between the actual tool and the patient's anatomy. Thus, as the detected position of the surgical tool changes within the three-dimensional space of the patient's anatomy, its representation on each image may be simultaneously updated in real time. The projected position of the surgical tool may be verified by touching the tool to the various fiducial markers and/or other known anatomical landmarks and confirming that the projected position of the surgical tool is within an acceptable degree of deviance, e.g., 1 mm, of the anatomical landmark reflected on each image.

According to embodiments, the exact dimensions of a powered driving device may be loaded into the image-guidance system. Thus, when a tip or an end of the powered driving device is touched to each fiducial marker, the image-guidance system may map the exact dimensions of the powered driving device into each image. Additionally, exact dimensions of specific implants, e.g., a screw, may be loaded into the image-guidance system. Upon selection of a particular implant, e.g., a particular sized screw (e.g., ranging from about 3.5 to 10 mm in diameter), the image guidance system may automatically simulate and project the dimensions of the particular sized screw onto each image. Further still, the image-guidance system may identify a specific orientation of the powered driving device, such that a calculated trajectory for an implant delivered by the powered driving device may be determined and simulated on the images. That is, upon determining the calculated trajectory, and with knowledge of the exact dimensions of the particular screw, the image-guidance system may simulate a predicted placement of the particular screw on the images. By altering the specific orientation of the powered driving device relative to the patient, the predicted placement of the particular screw may be recalculated and displayed until the clinician is satisfied with the predicted placement.

According to some embodiments, as discussed above, a surgical plan may be formulated pre-operatively such that a target position of a screw may be determined prior to surgery. During the surgery, according to embodiments, the surgeon may adjust an image-guided powered driving device until its calculated or virtual trajectory matches the target trajectory and a simulated screw placement matches the target position. According to embodiments, such adjustments of the powered driving device may also enable the clinician to identify a target insertion location in a selected bone for delivery of the screw into the target position.

The above-described image-guidance system may be provided by any suitable computing system, e.g., computing system 160, for executing imaging and/or simulation software, or any appropriate and useful imaging software variation. The computing system 160 may comprise a memory and one or more processors for executing the suitable imaging and/or simulation software. The memory may include computer-readable storage media for storing the suitable software that is executed by one or more processors. In an embodiment, the memory may include one or more solid-state storage devices such as flash memory chips.

In an alternative embodiment, the memory may be mass storage connected to the one or more processors via a communications bus, for example. Although the description of computer-readable storage media contained herein refers to a solid-state storage, computer-readable storage media may be any available media accessible by the one or more processors. Computer-readable storage media may include non-transitory, volatile and non-volatile, removable and non-removable media implemented in any method or technology for storage of information, e.g., computer-executable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to embodiments, computing system 160 may also contain communications connection(s), e.g., communication media, which allow the computing device to communicate with other devices. Communication media may embody computer-readable instructions, data structures, program modules, or other data in a modulated data signal, such as a carrier wave or other transport mechanism, and includes any information delivery media. The described communications connections and media are provided by way of example only and any suitable means of communicating between computer systems may be used within the spirit of the present disclosure.

Computing system 160 may also include input device(s), such as keyboard 165, and/or a mouse, pen, voice input device, touch input device, etc. (not shown). Output device(s), such as display 170, may also be included. The computing system 160 may operate in a networked environment using logical connections to one or more remote computing, input/output devices, etc., for example, neuro-monitoring apparatus 180, stereo camera apparatus 140, image display 150, etc. The logical connections between the computing system 160 and the remote devices may include a local area network (LAN), a wide area network (WAN), or any other suitable network. With reference to a LAN networking environment, the computing system 160 may be connected to the LAN through a network interface or adapter. With reference to a WAN networking environment, the computing system 160 may include a modem or other means for establishing communications over the WAN, such as the Internet. The described network connections are provided by way of example only and any suitable means of establishing a communications link between computer systems may be used.

The OR may also be equipped with neuro-monitoring apparatus 180. Intra-operative neuro-monitoring during a surgical procedure may include recording somatosensory evoked potentials (SSEP), motor evoked potentials (MEP), or electromyography (EMG). For example, the recorded data may be collected to detect indications of potential neurological compromise during the surgery. In general, a clinician may couple pairs of stimulating and recording electrodes via leads 185 to a plurality of primary muscle groups and to a computer system, e.g., laptop 190. Software executed by laptop 190 may selectively activate each stimulating electrode at specific intervals and may process and display the electrophysiologic signals as they are detected or registered by a corresponding recording electrode. As such, the clinician may observe and evaluate the electrophysiologic signals in real time during the surgery.

As may be appreciated, illustration and description of the various surgical devices and systems for performing surgical procedures are provided for purposes of explanation and example only. Indeed, any surgical devices and systems either now known or developed in the future for performing a spinal-fixation procedure may be used in combination with the disclosed powered driving device within the spirit of the present disclosure.

Figure 2:
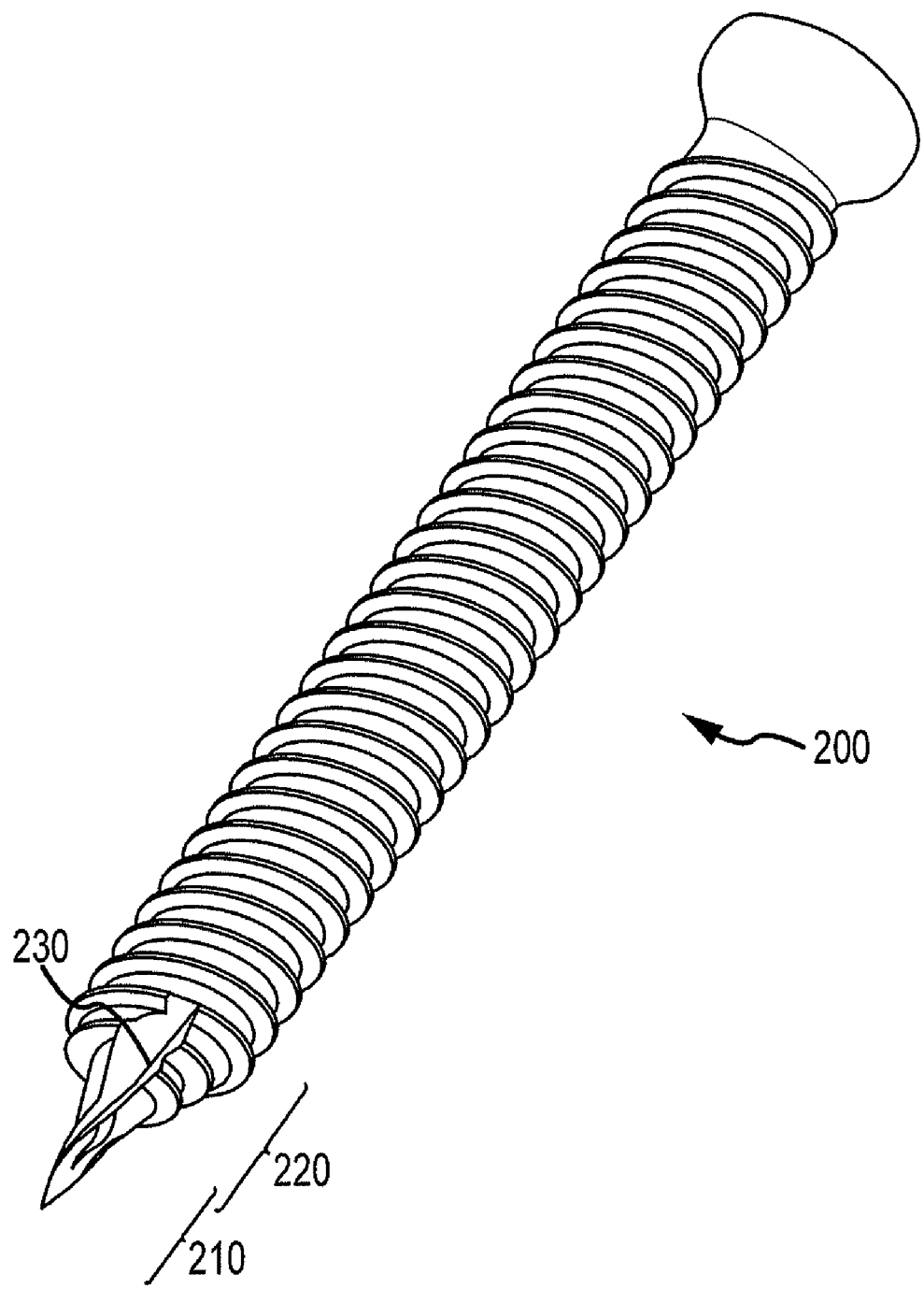
FIG. 2 is an illustration of a first embodiment of a specialized screw as described herein.

FIG. 2 is an illustration of a first embodiment of a specialized screw as described herein.

Specialized screw 200 illustrates a first embodiment of a specialized self-drilling, self-tapping screw. A specialized screw may refer to any suitable screw that may be used in combination with a powered driving device, as described herein, for insertion into bone. Further, suitable screws may or may not comprise each feature of the described embodiment, e.g., specialized screw 200, including described self-drilling and/or self-tapping features. That is, other suitable screw designs may be inserted into bone via a powered driving device as disclosed herein and may be included within the scope of the present disclosure.

According to embodiments, specialized screw 200 may be made of any suitable, non-toxic, material for insertion into a bone. Suitable materials may include, but are not limited to, titanium and stainless steel. Specialized screw 200 may further include a plurality of screw portions. For example, a first screw portion, e.g., tip portion 210, may implement a self-drilling function of specialized screw 200. Features of tip portion 210 may include a suitable degree of hardness such that embodiments of specialized screw 200 may easily penetrate the hard outer cortex of bone. Tip portion 210 may also exhibit a suitable degree of sharpness such that specialized screw 200 is prevented from skipping, rolling off, or walking off the bone in the absence of a pre-drilled guide hole. Tip portion 210 may further include any suitable shape or configuration such that specialized screw 200 embodies the disclosed self-drilling function.

According to embodiments, a second screw portion may also be provided, e.g., tapping portion 220. For example, tapping portion 220 may extend from within tip portion 210 into a threaded portion of specialized screw 200 and may facilitate a self-tapping function of specialized screw 200. Self-tapping enables embodiments of specialized screw 200 to accurately and easily advance through the self-drilled hole provided by tip portion 210. Further, tapping portion 220 may enable specialized screw 200 to cut and remove bone as it is placed or inserted, preventing specialized screw 200 from fracturing bone. Embodiments of tapping portion 220 may include a sharp cutting flute 230, running counter to screw threads 240 and roughly parallel to a length of specialized screw 200. According to embodiments, sharp cutting flute 230 may implement the self-tapping function of specialized screw 200. According to embodiments, the tapping portion 220 may further include any suitable configuration for accomplishing the disclosed self-tapping function.

As may be appreciated, illustration and description of the various features and functions associated with specialized screw 200 are provided for purposes of explanation and example only. Indeed, any compatible screw for use with a powered driving device for insertion into bone may be included within the spirit of the present disclosure.

Figures 3A, 3B:
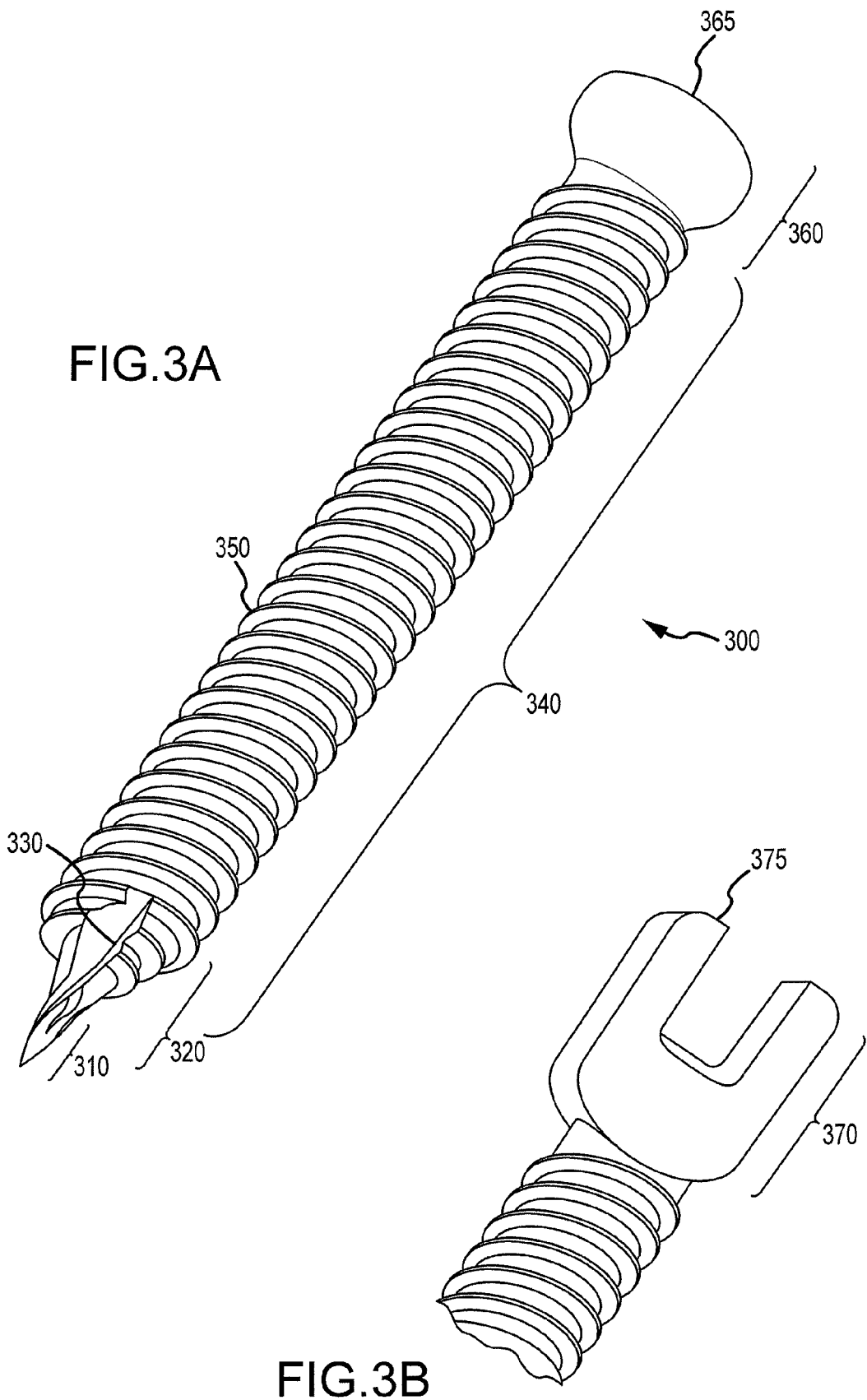
FIG. 3A is an illustration of a magnified embodiment of a specialized screw having a crown portion as described herein.
FIG. 3B is an illustration of a magnified embodiment of a specialized screw having an alternative crown portion as described herein.
Figure 3C:
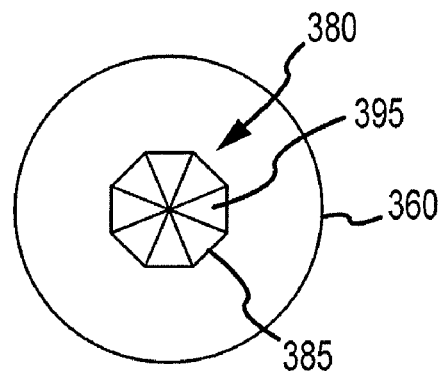
FIG. 3C is an illustration of a top view of an embodiment of a crown portion having a screw interface.
Figure 3D:
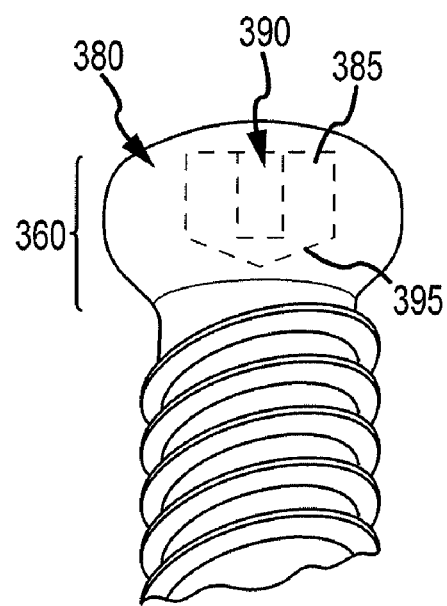
FIG. 3D is an illustration of a side view of an embodiment of a crown portion having a screw interface.

FIG. 3A is an illustration of a magnified embodiment of a specialized screw having a crown portion as described herein. FIG. 3B is an illustration of a magnified embodiment of a specialized screw having an alternative crown portion. FIG. 3C is an illustration of a top view of an embodiment of a crown portion having a screw interface. FIG. 3D is an illustration of a side view of an embodiment of a crown portion having a screw interface.

FIG. 3A is an illustration of a magnified embodiment of a specialized screw having a crown portion as described herein.

Similar to FIG. 2, FIG. 3A also illustrates a specialized self-drilling, self-tapping screw, e.g., specialized screw 300. As noted above, a specialized screw may refer to any suitable screw that may be used in combination with a powered driving device, as described herein, for insertion into bone. Further, suitable screws may or may not comprise each feature of the described embodiment, e.g., specialized screw 300, including described self-drilling and/or self-tapping features. That is, other suitable screw designs may be included within the definition of a specialized screw and may be inserted into bone via a powered driving device as disclosed herein.

The disclosed specialized screw 300 may also include a plurality of screw portions. For example, specialized screw 300 may include a tip portion, a tapping portion, a thread portion, and a crown portion. The tip portion of specialized screw 300, i.e., tip portion 310, may implement a self-drilling function of specialized screw 300. Features of tip portion 310 may include a suitable degree of hardness such that embodiments of the specialized screw 300 may easily penetrate the hard outer cortex of bone. For example, titanium or similar metal alloy may provide such suitable degree of hardness. The tip portion 310 may also exhibit a suitable degree of sharpness such that specialized screw 300 is prevented from skipping, rolling off, or walking off the bone in the absence of a pre-drilled guide hole. That is, the tip portion 310 may automatically create a guide hole when docked on bone by virtue of the suitable degree of sharpness. Indeed, according to embodiments, tip portion 310 may include any suitable shape or configuration such that the specialized screw 300 embodies the disclosed self-drilling function.

Embodiments of the specialized screw 300 may also include a tapping portion, i.e., tapping portion 320. Tapping portion 320 may refer to a portion of specialized screw 300 comprising a sharp cutting flute 330 that runs counter to screw threads and roughly parallel to a length of the specialized screw 300. The tapping portion 320 may extend from a region partially within tip portion 310 through a lower region of thread portion 340. That is, according to some embodiments, tapping portion 320 may span a plurality of lower screw threads that extend from tip portion 310, e.g., three lower screw threads. Sharp cutting flute 330 may implement a self-tapping function of specialized screw 300. Self-tapping enables embodiments of specialized screw 300 to accurately and easily advance through the self-drilled hole provided by tip portion 310. That is, sharp cutting flute 330 may enable embodiments of specialized screw 300 to cut and remove bone during insertion, preventing specialized screw 300 from fracturing bone. According to embodiments, tapping portion 320 may further include any suitable configuration for accomplishing the disclosed self-tapping function.

Embodiments of specialized screw 300 may also include thread portion 340. Thread portion 340 may include screw threads for engaging the bone and advancing the specialized screw 300. According to embodiments, the screw threads may comprise a single helical ridge 350 that spirals about thread portion 340 from tip portion 310 to just below crown portion 360. According to embodiments, helical ridge 350 may comprise a suitable degree of sharpness such that specialized screw 300 appropriately engages bone for secure placement. Additionally or alternatively, thread portion 340 may further include any suitable configuration for accomplishing the disclosed secure placement of specialized screw 300 into bone.

Embodiments of specialized screw 300 may further include a crown portion 360. Crown portion 360 may correspond to a top portion of specialized screw 300. Some embodiments of a crown portion may include a headless type crown (shown) or a fixed-head type crown (not shown).

FIG. 3B is an illustration of a magnified embodiment of a specialized screw having an alternative crown portion.

According to embodiments, crown portions may include headless type and fixed-head type crowns. For example, crown portion 360 embodies headless type crown 365, while alternative crown portion 370 embodies fixed-head type crown 375. According to embodiments, fixed-head type crown 375 may include an integrated apparatus for attaching a stabilizing rod following pedicle screw placement, for example. Alternatively, headless type crowns, e.g., headless type crown 365, may not comprise such integrated apparatus for attaching a stabilizing rod. Rather, after insertion of a headless type specialized screw, a cap configured for attaching a stabilizing rod may be coupled to headless type crown 365. As should be appreciated, embodiments of the powered driving device may be adapted for delivering a fixed head, a headless type, or any other compatible type of specialized screw 300.

FIG. 3C is an illustration of a top view of an embodiment of a crown portion having a screw interface.

According to embodiments, crown portion 360 (shown from top view) and alternative crown portion (not shown) may further include a suitable screw interface 380 for engaging a drive shaft interface of a powered driving device, as disclosed herein. As illustrated by the top view, according to embodiments, suitable screw interface 380 may include any common drive design, e.g., octagonal design 385 (shown), Robertson (square, not shown), hexed (not shown), Torx (star, not shown), etc., or may include any other suitable specialized drive design (not shown) for properly and securely engaging the drive shaft interface (not shown). According to some embodiments, suitable screw interface 380, having octagonal design 385 (shown) or other design (not shown), may further comprise a conical portion 395 for securely engaging and mating suitable screw interface 380 to the drive shaft interface (not shown).

FIG. 3D is an illustration of a side view of an embodiment of a crown portion having a screw interface.

As illustrated by the side view according to embodiments, suitable screw interface 380 may be provided as an aperture 390 (shown as dashed outline) within crown portion 360 (shown) or alternative crown portion (not shown). According to some embodiments, suitable screw interface 380, having octagonal design 385 (shown) or other design (not shown), may further comprise a conical portion 395 for securely engaging and mating suitable screw interface 380 to the drive shaft interface (not shown). As may be appreciated, suitable screw interface 380 may also include any other suitable portion (not shown) for securely engaging and mating suitable screw interface 380 to the drive shaft interface (not shown).

As may be appreciated, illustration and description of the various features and functions associated with specialized screw 300 are provided for purposes of explanation and example only. Indeed, any compatible screw for use with a powered driving device in a surgical procedure may be included within the spirit of the present disclosure.

Figure 4A:
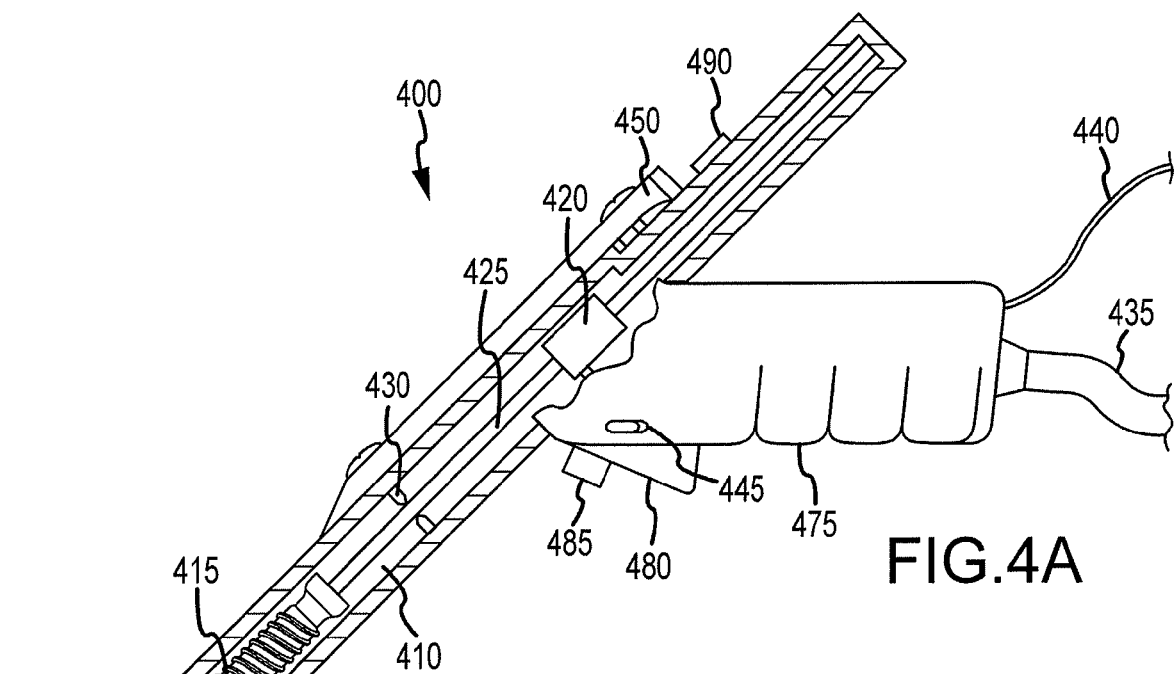
FIG. 4A is an illustration of a partial cross-sectional view of a first embodiment of a powered driving device as described herein.
Figure 4B:
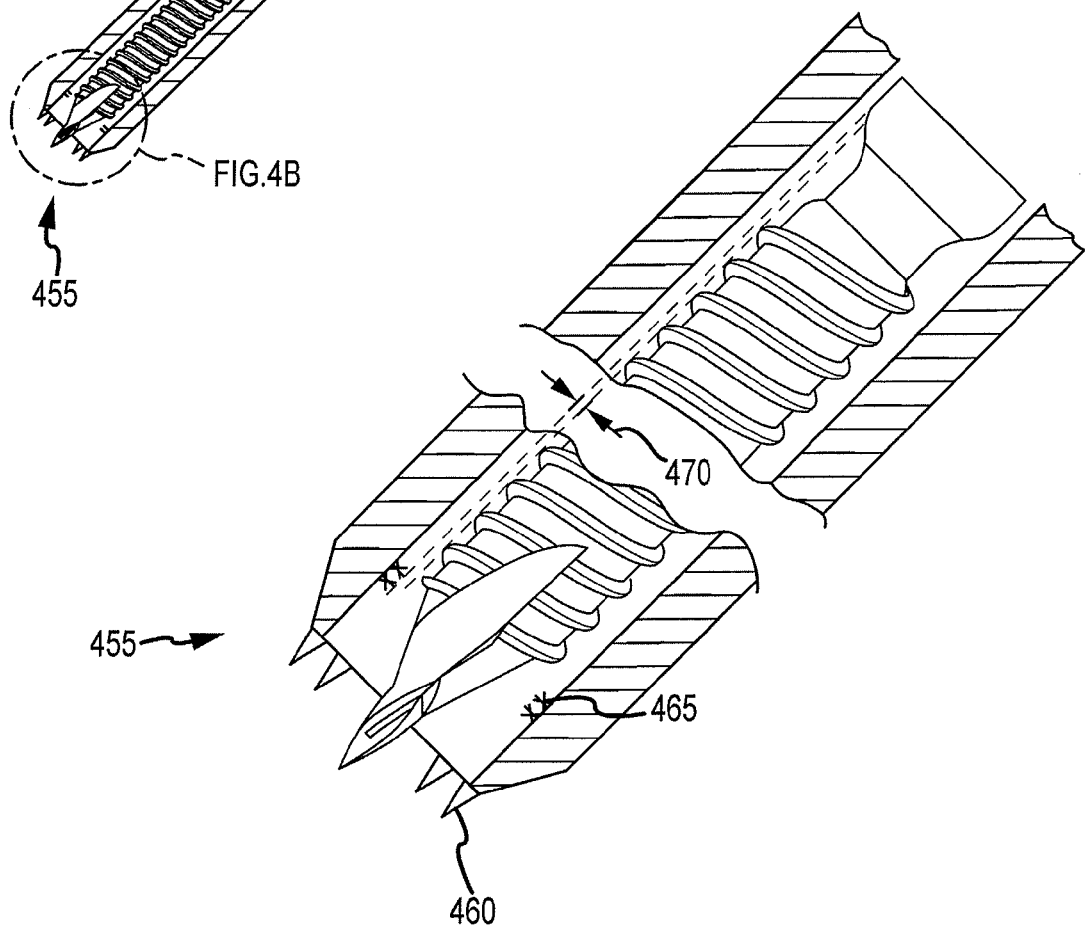
FIG. 4B is an illustration of a magnified, partial cross-sectional view of an embodiment of a powered driving device tip.

FIG. 4A is an illustration of a partial cross-sectional view of a first embodiment of a powered driving device as described herein. FIG. 4B is an illustration of a magnified, partial cross-sectional view of an embodiment of a powered driving device tip.

As illustrated in FIG. 4A, the powered driving device, e.g., powered driving device 400, may include any suitable powered driving device for accurately inserting a specialized screw into a bone. Powered driving device 400 may further comprise an elongated, cylindrical drive chamber 410. According to embodiments, drive chamber 410 may be configured to house a plurality of various specialized screw types and sizes, including various headless and fixed-head type and various length and diameter screws. That is, drive chamber 410 may be adjustable or otherwise suitable for accommodating various types and sizes of specialized screws. According to other embodiments, drive chamber 410 may be specifically manufactured for delivery of particular specialized screw types and size ranges, for example. According to this embodiment, a plurality of different sized powered driving devices may be manufactured corresponding to the particular specialized screw types and size ranges. According to embodiments, specialized screws may be loaded into drive chamber 410 and coupled to a drive shaft 425 via any suitable means.

According to embodiments, a position of the specialized screw 415 may be monitored by various systems and/or devices associated with the powered driving device 400. For example, a microcurrent-monitoring system, an image-guidance system, a bone-density monitoring system, a pressure-sensitive system, or any other suitable monitoring system may detect when specialized screw 415 is in an improper position near or contacting cortical bone and/or is oriented according to an improper trajectory.

According to embodiments, drive chamber 410 may be further configured, as discussed above, to deliver or pass an electric current, e.g., a microcurrent, to a specialized screw housed in drive chamber 410, e.g., specialized screw 415. For example, the microcurrent may be delivered via any suitable electric generator for providing voltage and may be passed by conductors 430 to drive shaft 425. According to some embodiments, the suitable electric generator may be provided at neuro-monitoring apparatus 180 and microcurrent may be passed to the powered driving device 400 via lead apparatus 440, for example. According to other embodiments, the suitable electric generator may be configured within the powered driving device 400.

According to alternative embodiments, delivering the microcurrent may be initiated via any suitable button, switch, etc. (not shown). For example, upon partial insertion of the specialized screw 415 into the bone, delivery of the microcurrent may be initiated. Partial insertion may correspond to a particular number of revolutions of the specialized screw 415 by the powered driving device, a particular depth of the specialized screw 415 as calculated by the image-guidance system, or any other predetermined threshold. According to some embodiments, microcurrent may be automatically initiated by the powered driving device upon detecting the predetermined threshold has been met. According to alternative embodiments, the microcurrent may be initiated when the powered driving device is appropriately docked onto the bone. According to other embodiments, the microcurrent may be initiated manually at the discretion of the clinician.

As described above, the microcurrent may be initiated by any suitable electric generator for providing voltage and may be passed by conductors 430 to drive shaft 425. According to embodiments, drive shaft 425 may comprise conductive properties and may thereby pass the microcurrent to specialized screw 415. According to embodiments, conductors 430 may take any suitable form such that a suitable electric connection may be provided between conductors 430 and drive shaft 425. Conductors 430 may be comprised of any type of conductive metal, metal alloy, or other suitable conductive material. For example conductors 430 may include metallic nodes (shown), wire brushes (not shown), etc.

According to alternative embodiments, drive chamber 410 may be made of a suitable non-conductive material and another component or apparatus (not shown) may be coupled to drive component 420, or otherwise, and may be configured to deliver microcurrent to specialized screw 415 via drive shaft 425, or otherwise.

According to further embodiments, lead apparatus 440 may be coupled to a neuro-monitoring apparatus, e.g., neuro-monitoring apparatus 180, for monitoring a microcurrent across the bone. For example, lead apparatus 440 may include an appropriate adapter and may be inserted into an appropriate receptacle of powered driving device 400, e.g., on handle portion 475. According to other embodiments, neuro-monitoring apparatus 180 may be coupled to powered driving device 400 via any suitable means. According to embodiments, a grounding lead may be attached at one end to a suitable location on the patient's body, e.g., the patient's abdominal area, and attached at another end to the neuro-monitoring apparatus 180. According to embodiments, the grounding lead may comprise a small-gauge needle or patch for affixing to the patient.

According to embodiments, upon partial insertion of the specialized screw 415 into the bone, e.g., a vertebral bone, a microcurrent delivered to specialized screw 415 may flow through or across the bone. As may be appreciated, composition of the vertebral bone may not be uniform and may include, inter alia, a less-resistive trabecular layer and a more-resistive cortical layer (see FIGS. 7B-7D for further illustration of bone layers). According to embodiments, the microcurrent may be represented according to the following electrical equation (Ohm's Law):

$$I = E/R$$

That is, where voltage (E) is constant, microcurrent (I) will decrease as resistance (R) increases. According to embodiments, microcurrent detected across the bone may change based on the resistance and/or density of the bone surrounding the specialized screw. For example, when the specialized screw is positioned within the internal trabecular layer, the microcurrent may register at about 20 mA. In the alternative, when the specialized screw is positioned near or within the dense cortical layer, i.e., in danger of traversing or fracturing the bone, the microcurrent may register at about 12 mA or less. According to further embodiments, if in fact the specialized screw traverses the bone, contacting tissue and/or nerves, microcurrent may register at 2 mA. That is, as the resistance of tissues and/or nerves may be considerably less that that of either the trabecular bone layer or the cortical bone layer, the microcurrent may easily pass through the nerve tissue. Thus, delivered microcurrent as low as 2 mA may register across nerve tissue. However, according to embodiments disclosed herein, shutdown of the powered driving device may preferably occur when the device comes in contact with the cortical bone, before it ever traverses and/or fractures the bone.

According to embodiments, the microcurrent may be monitored by various microcurrent monitoring systems, including monitoring apparatus within the powered driving device 400, the neuro-monitoring apparatus 180, or any other suitable microcurrent-monitoring system. According to alternative embodiments, resistance and/or voltage may be monitored and a microcurrent may be derived by any appropriate system according to Ohm's Law, as described above. As may be appreciated, according to some embodiments, the powered driving device 400 may include an internal ammeter (not shown), multimeter (not shown), or any other suitable device for measuring a microcurrent across a bone. Alternatively, neuro-monitoring apparatus 180 may monitor the microcurrent across the bone based on data passed via lead apparatus 440 and/or the grounding lead. Similarly, any other suitable microcurrent-monitoring system may be provided.

As will be discussed further herein, the powered driving device 400 may be automatically and substantially immediately shutdown when microcurrent across the bone registers below a predetermined threshold, e.g., at or below about 12 mA, indicative that specialized screw 415 may imminently traverse and/or fracture the bone. According to embodiments, breach of the predetermined threshold may be detected by neuro-monitoring apparatus 180, the internal ammeter, or other device, and may be communicated near instantaneously to a safety trigger component (not shown) for automatically shutting off powered driving device 400. Stated differently, fluctuations in microcurrent readings may be monitored and evaluated such that fluctuations below a predetermined threshold may initiate near-instantaneous automatic shutdown of the powered driving device 400.

Additionally or alternatively, continuous monitoring of the microcurrent while the specialized screw 415 is being advanced into the bone may be performed by neuro-monitoring apparatus 180 and/or the internal ammeter, for example. According to embodiments, during specialized screw placement, when the microcurrent is recorded within a predetermined range, e.g., a range between about 12 and 16 mA for example, an alert may be generated by an alert module 490 such that a clinician may be warned that specialized screw 415 may be approaching the cortical layer and/or that specialized screw 415 may have an improper trajectory. Alert module 490 may issue an alert via any suitable method, e.g., a visual alert and/or an audio alert, etc.

According to alternative embodiments, other suitable sensors or devices may be employed to monitor the position of a specialized screw (not shown). For example, other suitable devices may be employed to detect a bone density around the specialized screw. As a bone density of the cortical layer may be greater than a bone density of the trabecular layer, bone density may be used to indicate that a specialized screw is nearing the cortical layer and is in danger of traversing the bone (see FIGS. 7A and 7B for further illustration of bone layers). Alternatively, other suitable sensors may be employed to detect a proximity to the cortical bone layer via any other suitable means. For example, sonic devices, radar devices, pressure-sensitive devices, heat-sensitive devices, etc., may be employed to detect bone density and/or a proximity to the cortical bone layer. According to embodiments, upon any determination that the specialized screw may traverse the bone, the safety trigger component may automatically shutdown the powered driving device 400.

According to embodiments, drive shaft 425 may be mechanically or otherwise coupled to a drive component 420. Drive component 420 may provide a suitable force in the form of torque, or otherwise, via drive shaft 425 to a specialized screw housed in drive chamber 410. According to some embodiments, drive component 420 may provide controlled torque and/or rotations per minute (rpm) such that the specialized screw may not be rotated above a consistent, controlled predetermined rate. Drive shaft 425 may further include a drive shaft interface (not shown) for engaging a screw interface on the crown portion of specialized screw 415. Suitable force may be delivered by a pneumatic apparatus, hydraulic apparatus, spring apparatus, gear apparatus, or any other suitable force-delivery mechanism.

According to embodiments, the drive component 420 may be mechanically, electrically, or otherwise coupled to a suitable power source by power coupling apparatus 435. According to embodiments, power coupling apparatus 435 may comprise an electrical cord or a pressurized air hose, for example. According to alternative embodiments, power coupling apparatus 435 may be replaced by a battery pack or other suitable cordless power-delivery apparatus. According to alternative embodiments, power coupling apparatus 435 and lead apparatus 440 may be encased in a single insulated cord apparatus (not shown).

According to embodiments, the suitable power source may provide electrical (via an electrical cord or a battery pack), pneumatic (via a pressurized air hose), or other suitable power to the drive component 420 for delivering suitable force for insertion of the specialized screw 415 into bone. The suitable power source may be initiated by a power switch 445, by a pneumatic pedal or other suitable pneumatic initiation device (not shown), or by any other suitable power-initiation device. According to embodiments, the power switch 445 may be further configured to prevent accidental power-on or power-off. According to embodiments, the safety trigger component may be coupled to the power switch 445 to facilitate automatic shutdown of powered driving device 400. According to alternative embodiments, the safety trigger component may comprise an alternative power-off switch. In the case of electrical embodiments of the powered driving device, the electrical current utilized for powering the driving device may be adequately insulated from an internal ammeter and/or grounded apart from neuro-monitoring apparatus 180 such that microcurrent across the bone may be independently monitored and detected.

Powered driving device 400 may also be configured to include a tracking apparatus 450 (partially shown) enabling the image-guidance system to determine a location the of the powered driving device 400 and an orientation of the powered driving device 400 in real time. Tracking apparatus 450 may communicate an actual location of powered driving device 400 within the three-dimensional space of the image-guidance field to a computer system, e.g., computing system 160, by wired or wireless communication, as described above. That is, based on the orientation of the powered driving device 400 communicated by tracking apparatus 450, a predicted trajectory of the specialized screw 415 may be calculated and a simulated placement may be provided on image displays in real-time. That is, according to embodiments, when a powered driving device tip 455 is placed on or near a patient's skin, based on the exact dimensions of specialized screw 415, a simulated placement of the specialized screw may be calculated and displayed in real time, enabling a clinician to determine an appropriate incision location. Additionally or alternatively, during insertion of the specialized screw, a simulated placement of the specialized screw may be continuously re-calculated and displayed in real time, enabling a clinician to continually verify accurate placement of the specialized screw.

According to embodiments, as described above, powered driving device 400 may further include alert module 490. According to embodiments, alert module 490 may issue alerts regarding initial positioning while powered driving device 400 is being adjusted over a surgical site. That is, alert module 490 may indicate by a visual alert and/or an audio alert when powered driving device 400 is positioned in an appropriate docking location and oriented with a proper trajectory. For example, the alert module may issue a first alert, e.g., a yellow light, indicating that the powered driving device 400 is not positioned over a target insertion location and/or is not oriented according to a target trajectory. However, as the powered driving device 400 is adjusted about the surgical site, alert module 490 may issue a second alert, e.g., a green light, indicating that the powered driving device 400 is positioned over the target insertion location and is oriented according to the target trajectory. Thereafter, upon receiving an indication from alert module 490 that the powered driving device 400 is properly positioned, the powered driving device 400 may be docked onto the bone in the proper position.

According to other embodiments, the alert module 490 may provide various alerts regarding proper positioning of the specialized screw 415 while it is being delivered. According to embodiments, the alert module 490 may be provided in any suitable location on powered driving device 400 so as to communicate the various alerts to a clinician. For example, the alert module 490 may issue alerts when minor misalignments of the specialized screw are detected, e.g., an improper trajectory. For example, according to embodiments, the alert module 490 may receive microcurrent-monitoring data from the neuro-monitoring apparatus 180 and/or the internal ammeter indicating an improper position of specialized screw 415 within bone. As described above, an alert may be generated when a microcurrent is detected within a predetermined range, e.g., about 12-16 mA. Additionally or alternatively, the alert module may receive data regarding a virtual trajectory of the specialized screw 415 from the image-guidance system. For example, when the image-guidance system predicts that specialized screw 415 is advancing according to an improper trajectory that may not deliver specialized screw 415 into the target position, the alert module 490 may issue a warning to the clinician. As described above, according to embodiments, the alert module 490 may alert the clinician by any suitable method, for instance by an audible alert or by a visual alert on the image display and/or disposed on the powered driving device 400 itself. According to embodiments, alert module 490 may be communicatively coupled to the safety trigger component (not shown) and, when alert module 490 detects that the specialized screw 415 may imminently traverse and/or fracture the bone, the alert module 490 may substantially immediately command the safety trigger component to initiate shutdown of the powered driving device 400. According to alternative embodiments, alert module 490 and the safety trigger component may be comprised in a single component.

According to further embodiments, the alert module 490 may issue an alert when it detects malfunctions in the hardware and/or software of the image-guidance system, e.g., inconsistencies in a predicted or simulated placement and/or predicted or virtual trajectory of powered driving device 400.

Powered driving device 400 may also include a handle portion 475 that provides the clinician with an ergonomically adapted handle for stable, comfortable and effective use of the powered driving device 400 during an implantation procedure. According to embodiments, the handle may be configured in any appropriate orientation, e.g., angled roughly 35 degrees to 55 degrees from the drive chamber, roughly perpendicular to the drive chamber at about 90 degrees, or roughly linear to the drive chamber at about 180 degrees. The handle portion 475 may be further adapted to provide tactile signals to the clinician during placement procedures in order to provide additional verification feedback for accurate placement of the specialized screw.

Powered driving device 400 may further include a trigger drive 480. The trigger drive 480, or other suitable mechanism, may initiate insertion of the specialized screw 415. Particularly, the trigger drive 480 may induce drive component 420 to begin delivering force to the specialized screw 415. Trigger drive 480 may also be configured to simultaneously trigger the virtual image guidance display such that the clinician is provided with real-time virtual feedback regarding the orientation and advancement of specialized screw 415. Alternatively, trigger drive 480 may include a trigger guidance control 485 that may initiate image guidance upon demand when desired by the clinician. According to alternative embodiments, trigger guidance control 485 may be provided in a separate location from trigger drive 480. The trigger drive 480 may be further configured to provide safety components that prevent accidental triggering or shut off.

FIG. 4B is an illustration of a magnified, partial cross-sectional view of an embodiment of a powered driving device tip.

According to embodiments, powered driving device 400 may further comprise powered driving device tip 455, as described above. Powered driving device tip 455 may comprise docking teeth 460 and stop component 465. According to embodiments, docking teeth 460 may be configured to provide stabilization support for docking powered driving device 400 on an anatomical landmark or process. Specifically, powered driving device 400 may be docked on the bone in an appropriate insertion location for safely and accurately placing specialized screw 415 into a bone. According to embodiments, a tip portion of specialized screw 415, as properly loaded into drive chamber 410, may extend slightly beyond docking teeth 460. As such, according to embodiments, upon docking powered driving device 400, the tip portion of specialized screw 415 may automatically create a small impression, or guide hole, in the outer cortex of the bone by virtue of its suitably hard and sharp design and its extended position relative to the docking teeth 460. According to alternative embodiments, specialized screw 415 may be initially loaded into drive chamber 410 in a retracted position and, upon determination of an appropriate docking location and properly docking the powered driving device 400, the specialized screw 415 may then be extended. According to this embodiment, specialized screw 415 may be extended via a trigger control or any other suitable method and, upon extension, may create the small impression, or guide hole, in the outer cortex of the bone.

According to embodiments, stop component 465 may be provided for preventing counter-sinking of the specialized screw. That is, according to embodiments, stop component 465 may detect when a crown portion of the specialized screw reaches an end of the drive chamber 410 and may communicate with the safety trigger component or other appropriate component to automatically shutdown powered driving device 400. According to embodiments, stop component 465 may include a brush apparatus (shown), pressure sensor (not shown), magnetic sensor (not shown), or other suitable device for detecting the crown portion of the specialized screw. For example, as illustrated, the brush apparatus may be disposed so as not to come in contact with the screw until a wider crown portion reaches the end of the drive chamber 410. That is, a space 470 may be provided between the brush apparatus and the screw such that the space 470 prevents contact with the screw until the crown portion, which is wider than the space 470, reaches the end of drive chamber 410 and comes in contact with the brush apparatus. According to other embodiments, the crown portion may be comprised of an alternative type of metal detectable by a magnetic sensor, for example. Alternatively, stop component 465 may detect that the driver interface of drive shaft 425 has reached the end of drive chamber 410. According to embodiments, upon detection that the specialized screw crown portion and/or the drive shaft 425 have reached the end of drive chamber 410, stop component 465 may initiate automatic shutdown of powered driving device 400.

As may be appreciated, illustration and description of the various components and apparatuses associated with powered driving device 400 are provided for purposes of explanation and example only. Indeed, any suitable powered driving device for safely and accurately placing a specialized screw into a bone may be included within the spirit of the present disclosure.

Figure 5:
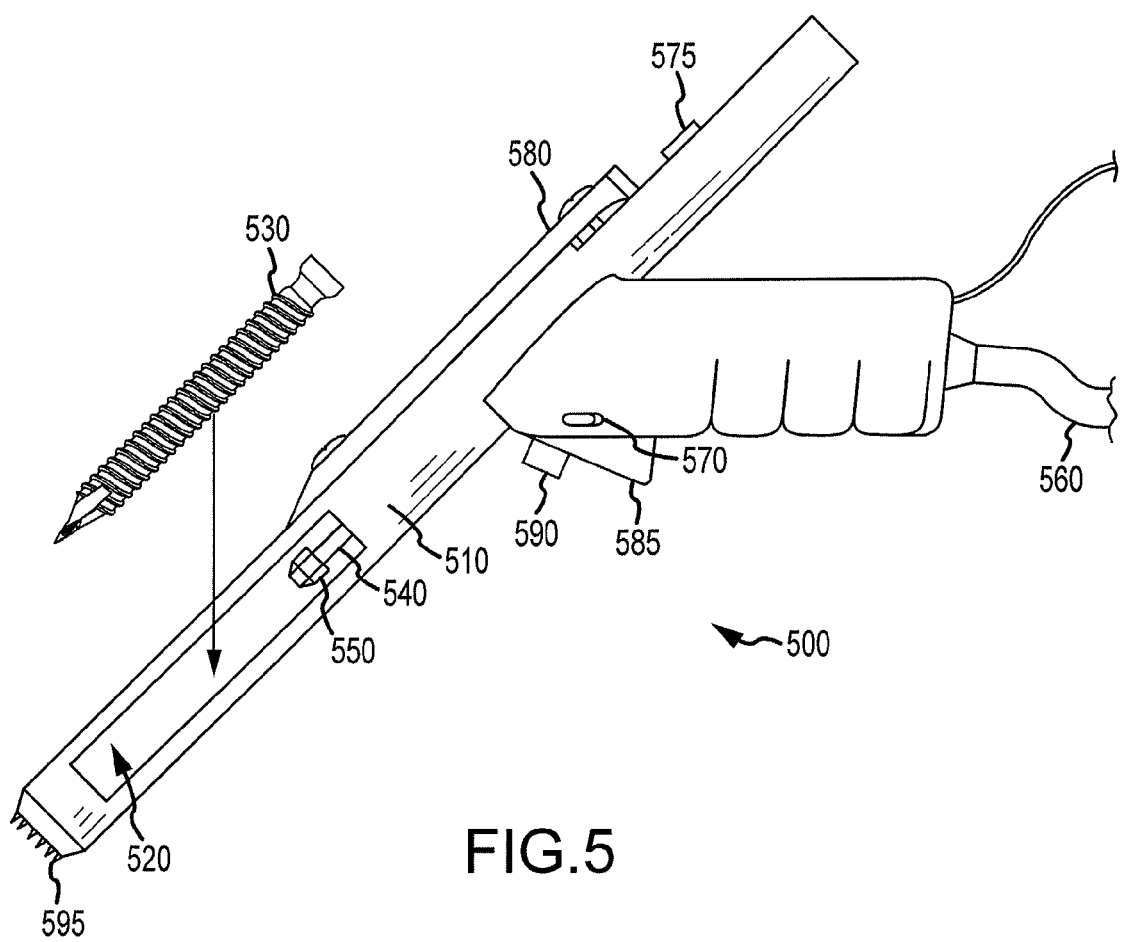
FIG. 5 is an illustration of a second embodiment of a powered driving device as described herein.

FIG. 5 is an illustration of a second embodiment of a powered driving device as described herein.

According to embodiments, the second embodiment of a powered driving device, e.g., powered driving device 500, may be substantially similar to powered driving device 400. According to some embodiments, FIG. 5 provides additional illustrative description for features not visible in FIG. 4.

According to embodiments, powered driving device 500 may comprise any suitable powered driving device for accurately inserting a specialized screw into a bone. As described above, powered driving device 500 may further comprise an elongated, cylindrical drive chamber 510. According to embodiments, drive chamber 510 may be adjustable or otherwise altered for accommodating various types and sizes of specialized screws, as with drive chamber 410. According to alternative embodiments, a plurality of different sized drive chambers 510 may be manufactured corresponding to particular specialized screw types and size ranges, for example. According to this embodiment, different sized drive chambers 510 may be interchanged and mechanically coupled to powered driving device 500 according to any suitable method.

According to further embodiments, drive chamber 510 may be configured with a loading aperture 520. Loading aperture 520 may be provided in any suitable location on powered driving device 500 such that a specialized screw, e.g., specialized screw 530, may be loaded into powered driving device 500. That is, loading aperture 520 may be provided on a side portion of powered driving device 500 (shown), a top portion of powered driving device 500 (not shown), a bottom portion of powered driving device 500 (not shown), or any other suitable location such that specialized screw 530 may be loaded into drive chamber 510 and coupled to drive shaft 540 via drive shaft interface 550.

As described above, powered driving device 500 may be docked onto a bone, e.g. medial to a transverse process of a vertebra of interest, upon confirming an appropriate insertion location and trajectory. Further, as described above, an appropriate specialized screw size having specific dimensions may be determined based on a simulated specialized screw placement from the docked location of powered driving device 500, e.g., calculated by the image-guidance system utilizing a "look-ahead" feature. Thereafter, according to embodiments, an appropriate specialized screw, e.g., specialized screw 530, may be loaded into drive chamber 510 via loading aperture 520 without undocking and/or reconfirming an appropriate insertion location and trajectory for powered driving device 500.

As discussed above, upon loading specialized screw 530, microcurrent may be delivered to specialized screw 530 via any suitable method. As may be appreciated, upon docking powered driving device 500 to bone and partially inserting specialized screw 530 into the bone, microcurrent may be delivered to specialized screw 530 and may flow across the bone. According to embodiments, fluctuations in microcurrent may be detected by the neuro-monitoring apparatus 180, an internal ammeter (not shown), or any other appropriate apparatus or device (not shown).

As discussed above, the powered driving device 500 may be automatically and substantially immediately shutdown when microcurrent across the bone registers below a predetermined threshold, e.g., at or below about 12 mA, indicative that specialized screw 530 may imminently traverse or fracture the bone. According to embodiments, during specialized screw placement, when the microcurrent is recorded within a predetermined range, e.g., a range between about 12 and 16 mA for example, an alert may be generated such that a clinician may be warned that specialized screw 530 may be approaching a cortical bone layer and/or may have an improper trajectory. As described above, any other appropriate sensor or device may be employed to monitor the position of a specialized screw (not shown) and to initiate automatic shutdown of powered driving device 500 when such appropriate device senses that specialized screw 530 may imminently traverse and/or fracture the bone.

As described above, drive shaft 540 may be mechanically or otherwise coupled to a drive component (not shown). According to embodiments, the drive component may provide a suitable force in the form of torque, or otherwise, via drive shaft 540 to a specialized screw housed in drive chamber 510. Drive shaft 540 may further include a drive shaft interface 550 for engaging a screw interface on the crown portion of specialized screw 530, for example. According to embodiments, drive shaft interface 550 may comprise any common drive design, e.g., octagonal (shown), Robertson (square, not shown), hexed (not shown), Torx (star, not shown), etc., or may include any suitable specialized drive design (not shown) for properly and securely engaging and mating with a suitable screw interface (not shown). According to some embodiments, drive shaft interface 550, having octagonal design (shown) or other design (not shown), may further comprise a conical portion for securely engaging and mating with a suitable screw interface, for example suitable screw interface 380 as described above. As may be appreciated, drive shaft interface 550 may also include any other suitable portion (not shown) for securely engaging and mating with a suitable screw interface.

According to embodiments, drive shaft interface 550 may be interchanged such that the powered driving device 500 may interface with a variety of screw interfaces. For example, drive shaft interface 550 may be exchanged via a quick-release coupling, a chuck apparatus, or otherwise.

As described above, the drive component may be mechanically, electrically, or otherwise coupled to a suitable power source by power coupling apparatus 560. According to alternative embodiments, power coupling apparatus 560 may be replaced by a battery pack or other suitable cordless power-delivery apparatus. According to further embodiments, a safety trigger component (not shown) may be coupled to the power switch 570 for facilitating automatic shutdown powered driving device 500. According to alternative embodiments, the safety trigger component may comprise an alternative power-off switch. In the case of electrical embodiments of the powered driving device 500, the electrical current utilized for powering the driving device may be adequately insulated from an internal ammeter and/or grounded apart from neuro-monitoring apparatus 180 such that microcurrent across the bone may be independently monitored and detected.

As described above, powered driving device 500 may also be configured with tracking apparatus 580 (partially shown). Tracking apparatus 580 may communicate an exact location of powered driving device 500 within the image-guidance field at all times.

As described above, powered driving device 500 may further include an alert module 575 for providing various monitoring and alarm functions within powered driving device 500. According to embodiments, alert module 575 may issue alerts regarding proper positioning while powered driving device 500 is being adjusted over a surgical site. According to other embodiments, the alert module 575 may provide various alerts regarding proper positioning of the specialized screw 530 while it is being delivered. According to further embodiments, alert module 575 may provide any other suitable alerts to a clinician via any suitable means during powered delivery of a screw into bone.

Further, as described above, powered driving device 500 may include a trigger drive 585 for initiating insertion of the specialized screw 530. Trigger drive 585 may also be configured to simultaneously trigger a virtual image guidance display such that the clinician is provided with real-time virtual feedback regarding the orientation and advancement of powered driving device 500 and specialized screw 530. Alternatively, trigger drive 585 may include a trigger guidance control 590 that may initiate image guidance upon demand when desired by the clinician.

According to embodiments as described above, powered driving device 500 may comprise docking teeth 595 and a stop component (not shown). According to embodiments, docking teeth 595 may be configured to provide stabilization support for docking powered driving device 500 on or near an anatomical landmark or process. Specifically, powered driving device 500 may be docked in an appropriate insertion location medial to a transverse process of a vertebra of interest such that, based on a projected trajectory and exact dimensions of specialized screw 530, specialized screw 530 may be properly inserted into a bone. As described above, the stop component may be provided for preventing counter-sinking of the specialized screw 530.

As may be appreciated, illustration and description of the various components and apparatuses associated with powered driving device 500 are provided for purposes of explanation and example only. Indeed, any suitable powered driving device for safely and accurately placing a screw into a bone may be included within the spirit of the present disclosure.

Figure 6:
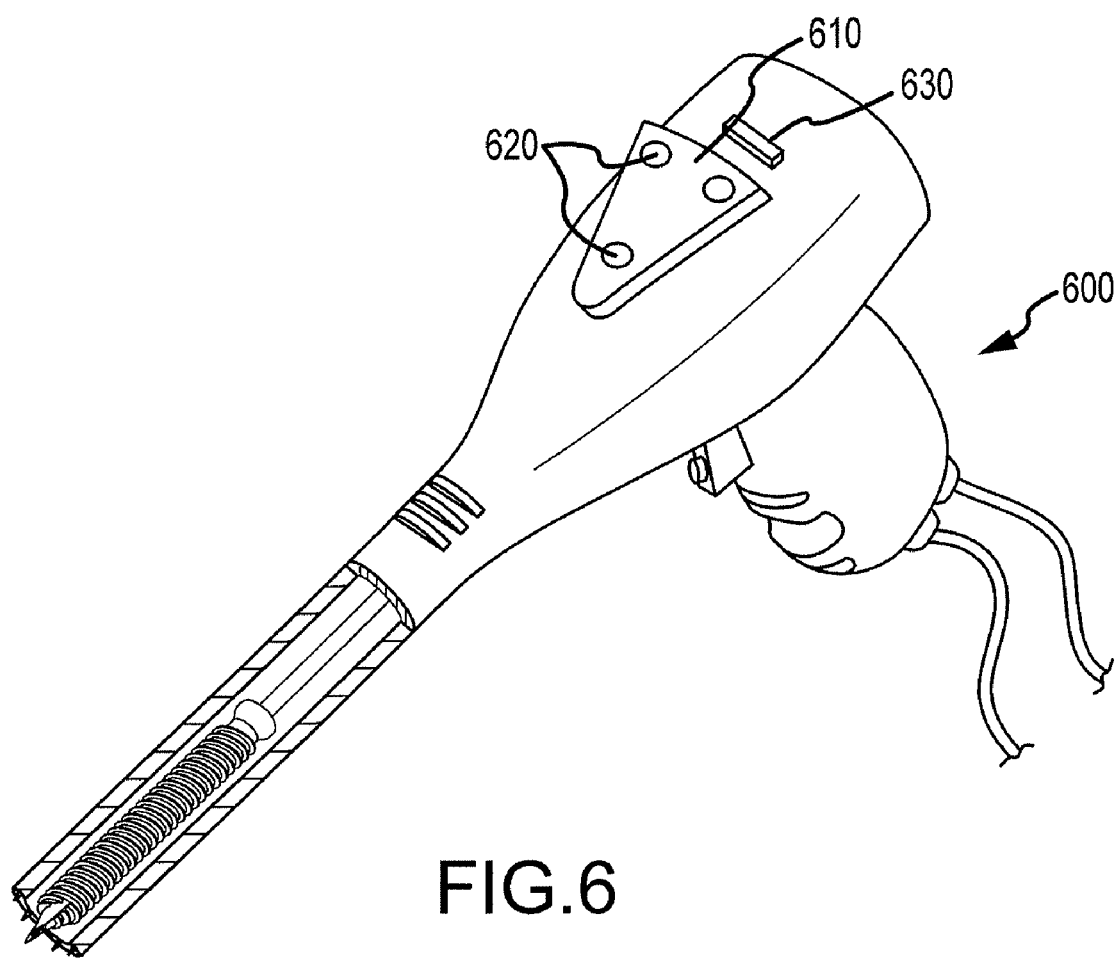
FIG. 6 is an illustration of a prospective, partial cross-sectional view of an embodiment of a powered driving device as described herein.

FIG. 6 is an illustration of a prospective, partial cross-sectional view of an embodiment of a powered driving device as described herein.

According to embodiments, the prospective view of an embodiment of a powered driving device, e.g., powered driving device 600, may be substantially similar to powered driving devices 400 and 500, as described above. According to some embodiments, FIG. 6 provides additional illustrative description for features not visible in FIGS. 4 and 5.

Specifically, an embodiment of a tracking apparatus 610 is illustrated. According to embodiments, tracking apparatus 610 may comprise a plurality of trackers, e.g., trackers 620. The plurality of trackers 620 may comprise any suitable number of trackers, e.g. three trackers 620 (shown). According to some embodiments, rather than a plurality of trackers 620, a single tracker 620 may be provided. As described above, trackers 620 may include any suitable tracking device for detection within an image-guidance field, e.g., light-emitting diodes (LEDs), mirror-like balls, electromagnetic coils, global positioning units, etc. The plurality of trackers 620 may be configured in any suitable array such that XYZ coordinates associated with the powered driving device 600 may be determined by the image-guidance system. For example, the locations of LED or mirror-like ball trackers 620 may be detected by stereo camera apparatus 140 and communicated to computing system 160 such that a location of the powered driving device 600 may be simulated in real time within image displays of the patient's anatomy.

According to embodiments, as described above, based on a location and orientation of tracked powered driving device 600 within three-dimensional space, the image-guidance system may calculate a trajectory of powered driving device 600 and a predicted or simulated placement of an associated specialized screw in real time. That is, at any time, upon docking the powered driving device 600 to bone and/or during insertion of the associated specialized screw, the image-guidance system may provide real-time feedback by continuously calculating a virtual trajectory and a simulated placement of the associated specialized screw as it is advanced into the bone.

As described above, powered driving device 600 may further include an alert module 630 for providing various monitoring and alarm functions of powered driving device 600. According to embodiments, alert module 630 may issue alerts regarding proper positioning while powered driving device 600 is being adjusted over a surgical site. According to other embodiments, the alert module 630 may provide various alerts regarding proper positioning of a specialized screw while it is being delivered.

As may be appreciated, illustration and description of an image-guidance system for use with the disclosed powered driving device is provided for purposes of explanation and example only. Indeed, within the spirit of the present disclosure, any image-guidance system either now known or developed in the future may be utilized in combination with the disclosed powered driving device for safely and accurately placing a screw into bone.

Figure 7C:
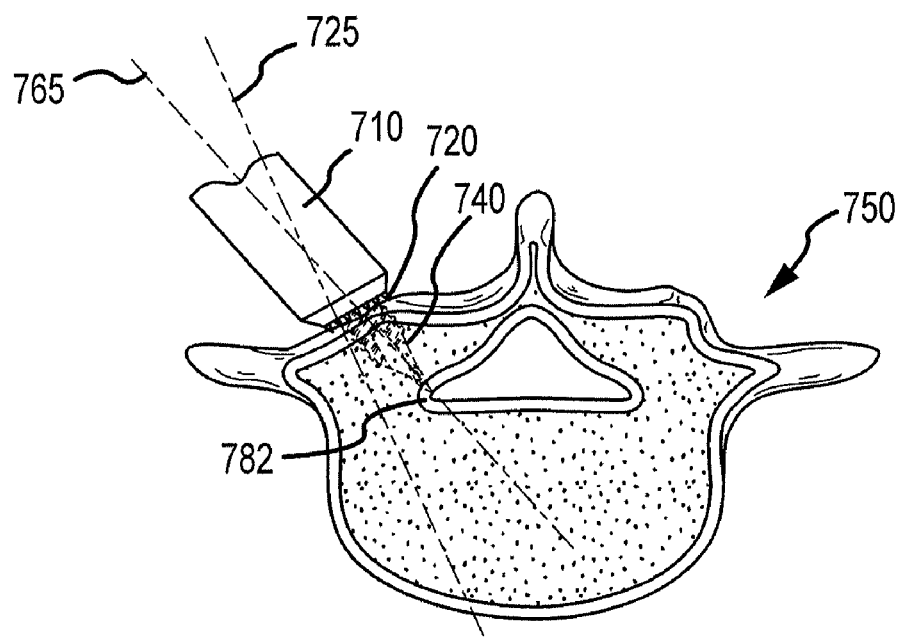
FIG. 7C is an illustration of an axial view of a first improperly placed screw in a pedicle as described herein.
Figure 7D:
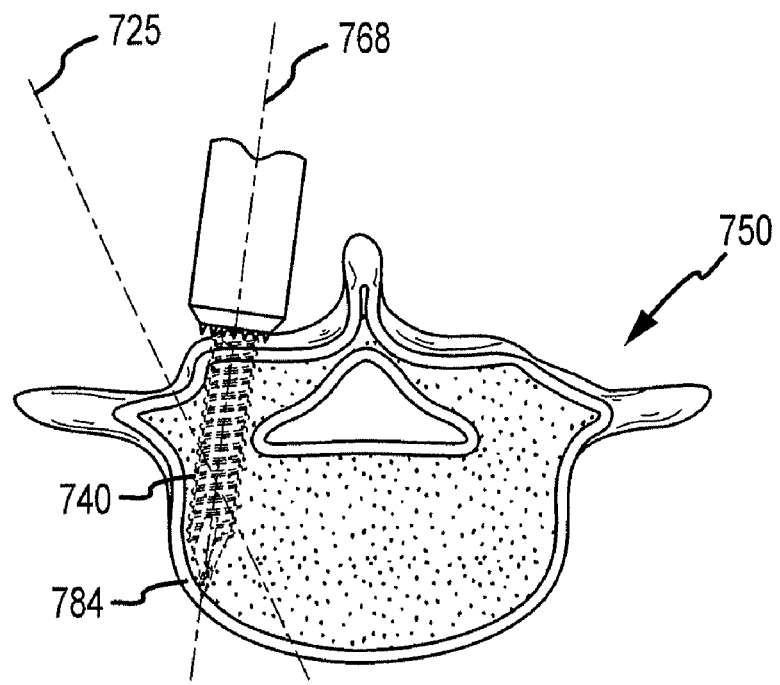
FIG. 7D is an illustration of an axial view of a second improperly placed screw in a pedicle as described herein.

FIG. 7A is an illustration of a sagittal view of an embodiment of a properly placed screw in a pedicle as described herein. FIG. 7B is an illustration of an axial view of an embodiment of a properly placed screw in a pedicle as described herein. FIG. 7C is an illustration of an axial view of a first improperly placed screw in a pedicle as described herein. FIG. 7D is an illustration of an axial view of a second improperly placed screw in a pedicle as described herein.

FIG. 7A is an illustration of a sagittal view of an embodiment of a properly placed screw in a pedicle as described herein.

As described above, an image-guidance system may be deployed by placing a stationary tracker on a spinous process near a surgical site, for example, spinous process 760 or other adjacent spinous process. Thereafter, a powered driving device 710 may be registered within the image-guidance system. According to embodiments, the powered driving device 710 may be docked via docking teeth 720 in an appropriate location for inserting a specialized screw through a pedicle 730 of vertebra 750. For example, the powered driving device 710 may be docked on the exterior of the vertebra, e.g., on a lamina medial to a transverse process, e.g., transverse process 785. Thereafter, according to embodiments described herein, a specialized screw may be inserted into the pedicle 730 by powered driving device 710, e.g., specialized screw 740. For illustrative purposes, pedicle 745 corresponds to a pedicle of adjacent vertebra 755.

FIG. 7B is an illustration of an axial view of an embodiment of a properly placed screw in a pedicle as described herein.

As described above, according to embodiments, the powered driving device 710 may be docked via docking teeth 720 in an appropriate location for inserting a specialized screw into a pedicle 730, e.g., medial to a transverse process 785. As illustrated, pedicle 730 corresponds to one of a pair of narrow bone channels, or roots, of a vertebral arch that connect a lamina 775 to a vertebral body 795 of vertebra 750. Pedicle 735 refers to the other pedicle of the pair of pedicles of vertebra 750.

As illustrated, the narrow channel of bone corresponding to pedicle 730 is provided between a spinal canal 790 that houses the spinal cord and a lateral exterior of the vertebra. According to embodiments described herein, a specialized screw 740 may be inserted through cortical bone layer 780 into lamina 775, through pedicle 730, and into vertebral body 795, where proper placement may be accomplished. As may be appreciated, there is minimal allowance for error in placing specialized screw 740 through pedicle 730 because pedicle 730 may only be a few millimeters wider than specialized screw 740.

According to embodiments, target trajectory 725 may be calculated. Target trajectory 725 corresponds to a trajectory that is calculated to deliver specialized screw 740 into a target position, as described above. As illustrated, when the specialized screw 740 follows target trajectory 725, the specialized screw 740 may be properly delivered into a target position through lamina 775, through pedicle 730, and into vertebral body 795 within a trabecular bone layer 770.

As illustrated by the axial view of vertebra 750, the cortical bone layer 780 is provided on exterior surfaces of vertebra 750 and adjacent to spinal canal 790. Thus, according to embodiments described herein, when microcurrent monitoring or other sensory device detects that a tip of specialized screw 740 is in contact with cortical bone, this may indicate that the specialized screw 740 is in danger of breaking into the spinal canal 790. For example, a microcurrent may register at or below about 12 mA when the specialized screw 740 is near or contacting cortical bone. As described above, if the specialized screw 740 contacts the spinal cord, serious harm to a patient may result, including paralysis or death.

Also illustrated in the axial view is trabecular bone layer 770, which refers to the spongy bone on an interior of the vertebra 750 and surrounding specialized screw 740 when it is properly placed. According to embodiments described herein, when microcurrent monitoring or other sensory device detects that specialized screw 740 is in contact with trabecular bone a clinician may verify that the specialized screw 740 is properly advancing through a pedicle and into a vertebral body. For example, a microcurrent may register at or about 20 mA when the specialized screw 740 is within trabecular bone layer 770.

FIG. 7C is an illustration of an axial view of a first improperly placed screw in a pedicle as described herein.

As described above, according to embodiments, the powered driving device 710 may be docked via docking teeth 720 onto an improper location for inserting a specialized screw into a pedicle 730 of vertebra 750. That is, when powered driving device 710 is docked onto improper location, the specialized screw 740 may be directed via improper trajectory 765. According to embodiments described herein, an appropriate insertion location may be determined based on an alert indication from powered driving device 710. However, based on clinician error or otherwise, powered driving device 710 may be docked onto an improper location.

As described above, when specialized screw 740 advances according to improper trajectory 765, the powered driving device 710 may issue an alert or otherwise, as described above. According to further embodiments, if specialized screw 740 continues advancement according to improper trajectory 765, the powered driving device 710 may detect that the specialized screw 740 may imminently contact, breach, and/or fracture cortical bone, e.g., medial cortical bone 782. If it is determined that specialized screw 740 may imminently breach and/or fracture cortical bone, the powered driving device 710 may be automatically shutdown, as described herein.

FIG. 7D is an illustration of an axial view of a second improperly placed screw in a pedicle as described herein.

As described above, according to embodiments, the powered driving device 710 may be docked via docking teeth 720 onto an improper location for inserting a specialized screw into a pedicle 730 of vertebra 750. That is, when powered driving device 710 is docked onto an improper location, the specialized screw 740 may be directed via improper trajectory 768.

As described above, when specialized screw 740 advances according to improper trajectory 768, the powered driving device 710 may issue an alert or otherwise, as described above. According to further embodiments, if specialized screw 740 continues advancement according to improper trajectory 768, the powered driving device 710 may detect that the specialized screw 740 may imminently contact, breach, and/or fracture cortical bone, e.g., lateral cortical bone 784. If it is determined that specialized screw 740 may imminently breach and/or fracture cortical bone, the powered driving device 710 may be automatically shutdown, as described herein.

Figure 8:
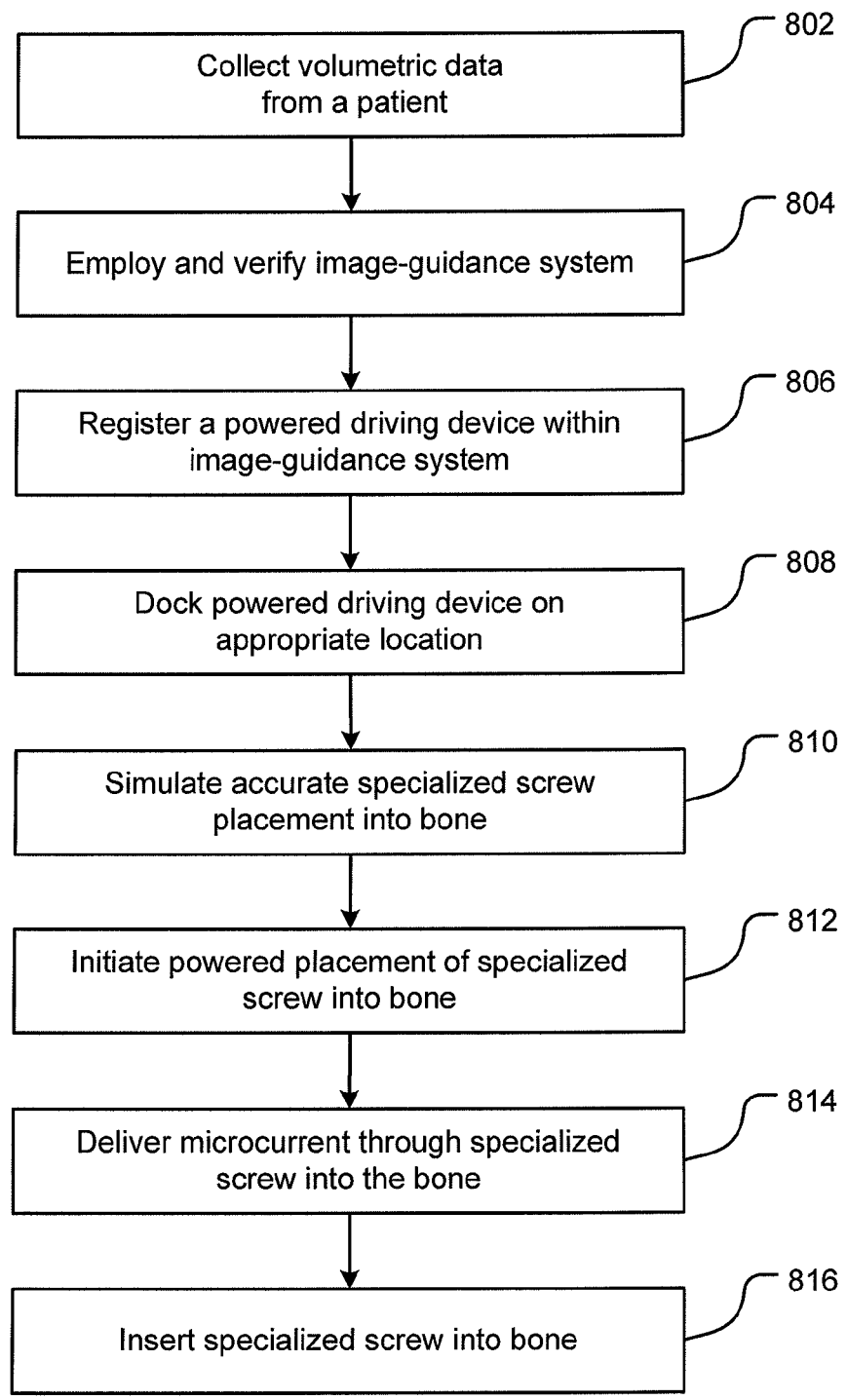
FIG. 8 is a flow-diagram illustrating an embodiment of a method for placing a screw into a bone using a powered driving device.

FIG. 8 is a flow-diagram illustrating an embodiment of a method for placing a screw into a bone using a powered driving device.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

At collect volumetric data operation 802, two-dimensional and/or three-dimensional volumetric data may be collected from a patient. Embodiments of the present disclosure include collecting volumetric data using an X-ray device, such as a fluoroscopic device that may obtain a plurality of X-rays while rotating about 190 degrees within the patient. Other embodiments may involve an intra-operative CT scanning device that may provide a plurality of image displays.

According to embodiments, the volumetric data may then be loaded into an image-guidance system and converted into a plurality of three-dimensional images. As may also be appreciated, pre-operative imaging data collected from the patient may also be employed within the image-guidance system. For example, the image-guidance system may include a display having a plurality of views for providing imaging data from various sources to a clinician, e.g. pre- and intra-operative images including images generated via X-ray, CT, MRI, etc. In addition, the image-guidance system may project a position of a powered driving device and/or a specialized screw onto each of the displayed plurality of views.

At employ and verify operation 804, an image-guidance system may be employed and verified according to any suitable method. According to embodiments, any suitable image-guidance system either now known or later developed may be utilized for placing a screw into bone with the disclosed powered driving device. For example, according to embodiments, an image-guidance system may be employed using active infrared technologies, e.g. via a stationary LED tracker affixed to a spinous process of the patient, or other technologies presently available or disclosed in the future for mapping the plurality of two- and three-dimensional images to the three-dimensional space of the patient. For example, as described above, locations of LED or mirror-like ball units on the stationary tracker may be detected by stereo camera apparatus 140 and communicated to computing system 160 such that a location of the spinous process in three dimensional space may be mapped to a corresponding location of the spinous process within the image displays.

As described above, upon generating the image-guidance field, verification of the image-guidance system may be performed. Any suitable verification method may be employed and embodiments may include utilizing a probe, or other suitable device, to register the infrared field generated by the image guidance system. According to embodiments, the probe may comprise a tracking apparatus such that the image-guidance system may detect an actual location and orientation of the probe within three-dimensional space. Further, a virtual location of the probe may be calculated and simulated within the image displays of the patient's anatomy.

According to embodiments, the image-guidance field may be verified using a plurality of fiducial markers as reference points within the three-dimensional space of the patient. Specifically, fiducial markers may refer to any suitable anatomical landmark or other feature that may be visually recognized by the clinician within the three-dimensional space of the patient's anatomy and within the image displays of the patient's anatomy. According to embodiments, when the probe is touched to each of the plurality of fiducial markers, the projection of the probe's location within the image displays should be reflected on or near images of each fiducial marker to within an acceptable degree of deviance, e.g., 1 millimeter. In the case of an unacceptable degree of image deviance, a point-to-point registration may be used to recollect imaging data. Once accuracy of the image-guidance system is established, a probe may be touched to other known anatomical features and landmarks associated with an area of interest specific to a particular surgical procedure, again confirming the accuracy of the image-guidance system.

At registration operation 806, a powered driving device may be calibrated or registered within the image-guidance system. The powered driving device may be any suitable device having the features described herein, as described above. Particularly, the powered driving device may be configured with a tracking apparatus, as described above, such that it may be registered within the image-guidance field.

According to embodiments, upon activation of the tracking apparatus (or upon automatic activation), a location and orientation of the powered driving device may be detected and reflected on image displays of the patient's anatomy. According to embodiments, and similar to the verification method described above, the powered driving device may be touched to each of the plurality of fiducial markers in order to verify that the projection of the powered driving device's location within the image displays is reflected on or near images of each fiducial marker (e.g., to within 1 millimeter acceptable deviance).

At docking operation 808, the registered powered driving device may be utilized on a surface of the patient's skin, or on any other suitable anatomical surface, to locate an appropriate docking location. According to embodiments, registered powered driving device may be used to identify a specific anatomical landmark of interest based on a virtual location of the powered driving device on the image displays. For example, a particular pedicle of interest may be located. Further embodiments include marking on the surface of the patient's skin the particular location of the pedicle and a corresponding anatomical location for placement of the specialized screw. As described above, the powered driving device may further provide an alert such that a clinician may be directed by the device to an appropriate insertion location. That is, a visual and/or audio indication may communicate that the powered driving device is positioned over the appropriate insertion location. Thereafter, according to embodiments, a small incision may be made in the patient's skin and the powered driving device may be advanced through the incision and an appropriate docking location may be determined.

According to embodiments, an appropriate docking location may be determined by adjusting the powered driving device about a surgical site. According to some embodiments, the powered driving device may provide an alert when the powered driving is positioned over an appropriate insertion location and when the powered driving device is oriented according to an appropriate trajectory. That is, embodiments allow for determination of an appropriate location for docking the powered driving device based on visual anatomical landmarks and/or feedback from the image-guidance system. Further, embodiments allow for determination of the appropriate trajectory for delivering the specialized screw into a target location based feedback from the image-guidance system, for example. Specifically, the powered driving device may include a location feedback component that allows a suitable software application, as discussed below, to receive a location of a tip and an orientation of the powered driving device in three-dimensional space from a tracking apparatus at all times. According to embodiments, the tracked location and orientation of the powered driving device may be used to calculate a virtual position and trajectory of the powered driving device on image displays at all times. According to embodiments, powered driving device may detect and communicate when the virtual trajectory of the specialized screw matches a target trajectory for proper placement of the specialized screw into a target position. When a clinician confirms that the insertion location and the trajectory of the powered driving device are appropriate for properly placing the specialized screw into the target position, the powered driving device may be docked onto the bone.

That is, the powered driving device may be docked near a selected anatomical landmark, such as a transverse process of the spine. As should be appreciated, any method or process, whether manual or otherwise, for determining an appropriate insertion location for docking the powered driving device is well within the present disclosure. Embodiments of the present methods may include image-guided, visual, and/or tactile placement of the powered driving device onto the selected anatomical landmark such that accurate docking is achieved. Further embodiments include re-verifying imaging accuracy by undocking the driving device from the selected anatomical landmark and touching various portions of the selected anatomical landmark that may be visually, tactilely, or otherwise recognized and verified. For example, the driving device may be selectively placed on top of a transverse process of interest, on bottom of the transverse process, and then onto the middle of the transverse process.

Further embodiments may include docking teeth on a tip of the powered driving device for stabilizing placement and preventing slippage during docking of the powered driving device onto the selected anatomical landmark. As may be appreciated, upon proper docking of the powered driving device on the bone, a self-drilling tip portion of a specialized screw may contact and automatically create a small impression, or guide hole, in the outer cortex of the bone. That is, according to some embodiments, upon proper docking of the powered driving device onto the bone, the tip of the specialized screw may be at least partially disposed within the hard outer cortex of the bone. According to alternative embodiments, the specialized screw may be initially loaded into the drive chamber in a retracted position and, upon properly docking the powered driving device onto the bone the specialized screw may be extended. According to this embodiment, upon extension of the specialized screw, the specialized screw may create the small impression, or guide hole, in the outer cortex of the bone.

At simulate operation 810, any suitable type of suitable simulation or imaging software may be employed. The suitable software may be configured so as to simulate placement of the specialized screw based on exact dimensions of the specialized screw and a virtual trajectory of the powered driving device. For example, as discussed above, the suitable software may relay real-time location feedback, in the form of a three-dimensional display or otherwise, regarding the location and orientation of the powered driving device, the specialized screw, or both. As described above, the a calculated or virtual location and orientation of the powered driving device may be reproduced on image displays of the patient's anatomy, i.e., the simulated location of the powered driving device may be provided within the display images of the bones and anatomical landmarks of the patient's anatomy.

For example, embodiments of the present disclosure may allow the clinician to input a particular make, type, or size of the specialized screw into the suitable software such that the precise length and diameter of the screw is accounted for in the display imagery. Alternative embodiments of the present disclosure may enable the powered driving device to detect the size and type of the specialized screw and to automatically relay that data to the suitable software. As such, as the clinician makes minor adjustments in the orientation of the powered driving device, which are automatically communicated to the suitable software, revised trajectories and depth calculations for the specialized screw may be automatically displayed. The clinician may make any number of appropriate adjustments while monitoring the display in order to direct the precise placement of the specialized screw into a target position (to within 1 millimeter of accuracy, for example).

The suitable software may be further configured to comprise different modules or components that may provide different aspects of the visual display and different types of useful and appropriate data for use in accurately placing a bone screw. As described above, embodiments of the disclosed methods may employ any suitable computing system for executing the disclosed suitable software, or any appropriate and useful variation of the disclosed suitable software.

At initiate operation 812, after final verification of the predicted placement of the specialized screw, the powered driving device may be initiated. Initiation of the driving device may be made by any suitable trigger drive. According to embodiments, the trigger drive may be configured to prevent accidental initiation and/or shutdown of the powered driving device. Following initiation of the powered driving device, real-time feedback from the image guidance system may continue such that the clinician may view a simulated specialized screw on the image display as the actual specialized screw is being inserted into the bone. Further, embodiments may also allow for an automatic shutdown of the powered driving device if the virtual screw is projected to breach the bone by the image-guidance system. As such, this embodiment may allow for automatic shutdown of the driving device even prior to a microcurrent-monitoring automatic-shutdown feature, as described below, providing an additional layer of protection against potential inaccurate placement of the screw.

At deliver operation 814, a microcurrent, e.g., in mA, may be passed through the specialized screw and into the bone. As described above, the microcurrent may be automatically initiated upon partial insertion of the specialized screw based on a predetermined threshold. According to alternative embodiments, the microcurrent may be initiated when the powered driving device is appropriately docked onto the bone. Alternatively, microcurrent may be manually initiated based on clinician discretion. As will be recognized by those skilled in the art, microcurrent may be passed into the specialized screw by any suitable method, including but not limited to, microcurrent passed along the interior walls of the driving device and establishing any suitable electrical connection with a drive shaft coupled to the specialized screw or to the specialized screw itself. Alternately, microcurrent may be delivered directly to a crown portion of the specialized screw and the walls of the driving device may be constructed of any suitable non-conductive material.

Embodiments of the present systems may utilize fluctuations in the microcurrent for providing a fail-safe feature and/or an alert feature. For example, as described above, the powered driving device may be automatically and substantially immediately shutdown when the microcurrent across the bone registers below a predetermined threshold, e.g., at or below about 12 mA, indicative that specialized screw may imminently traverse and/or fracture the bone. According to other embodiments, during specialized screw placement, when the microcurrent registers within a predetermined range, e.g., a range between about 12 and 16 mA for example, an alert may be generated such that a clinician may be warned that specialized screw may be approaching the cortical layer and/or may be oriented according to an improper trajectory.

At insertion operation 816, a specialized screw may be placed into the bone of interest. Specifically, the image-guidance data may be fed into the suitable software to provide real-time feedback while the specialized screw is being inserted into the bone. In contrast to previous methods and systems, the clinician may monitor the three-dimensional image display during screw insertion, which relays a virtual trajectory of the driving device and/or simulated advancement of the specialized screw in real-time to the clinician. As such, the present methods may provide immediate, precise feedback moment-by-moment during a surgical procedure. Embodiments of the present methods provide accurate placement of a specialized screw into a bone of the spine, for example. Other embodiments of the present systems may include the accurate placement of any compatible screw into an appropriate bone.

As may be appreciated, description of a method for placing a screw into a bone using a powered driving device is provided for purposes of explanation and example only. Indeed, although the method is described as a series of steps, each step should not be understood as a necessary step, as additional and/or alternative steps may be performed within the spirit of the present disclosure. Additionally, described steps may be performed in any suitable order and the order in which steps were described is not intended to limit the method in any way.

Figure 9:
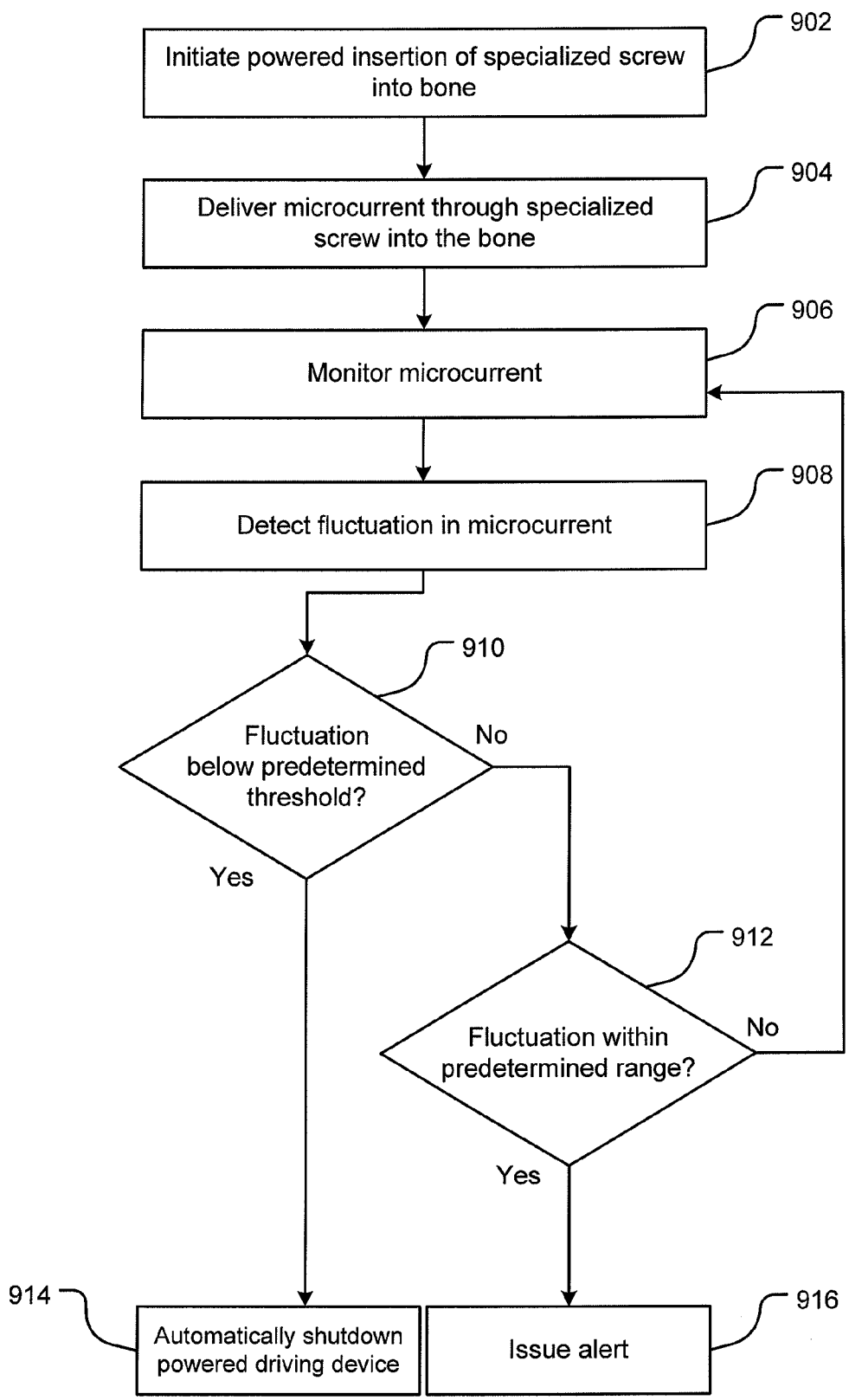
FIG. 9 is a flow-diagram illustrating a first embodiment of a method for automatically shutting down a powered driving device during screw placement.

FIG. 9 is a flow-diagram illustrating a first embodiment of a method for automatically shutting down a powered driving device during screw placement.

At initiate operation 902, after verification of a predicted placement of the specialized screw using the image-guidance system or otherwise, the powered driving device may be initiated, as described above. Following initiation of the powered driving device, real-time feedback from the image-guidance system may continue such that the clinician may view a simulated specialized screw on the image display as the actual specialized screw is being inserted into the bone At deliver operation 904, a microcurrent, e.g., in mA, may be passed through the specialized screw and into the bone. As described above, microcurrent may be automatically initiated upon partial insertion of the specialized screw based on a predetermined threshold. According to alternative embodiments, the microcurrent may be initiated when the powered driving device is appropriately docked onto the bone. Alternatively, microcurrent may be manually initiated based on clinician discretion. As will be recognized by those skilled in the art, microcurrent may be passed into the specialized screw by any suitable method.

At monitor operation 906, fluctuations in the microcurrent may be monitored to provide a fail-safe feature and/or an alert feature. As may be appreciated, composition of a bone may not be uniform and may include, inter alia, a less resistive trabecular layer and a more resistive cortical layer. According to embodiments, detected microcurrent may fluctuate based on the resistance of the bone surrounding the specialized screw. As such, monitoring fluctuations in the microcurrent provides an indication of whether the specialized screw is properly positioned in the trabecular layer, or improperly positioned in contact with the cortical layer. According to embodiments, microcurrent monitoring may be conducted by an internal ammeter or other device of the powered driving device or may be conducted by a neuro-monitoring apparatus.

At detect operation 908, a fluctuation in the microcurrent may be detected. That is, as the microcurrent may generally register at roughly 20 mA when the specialized screw is within the trabecular layer, a fluctuation may be detected when the microcurrent registers below about 20 mA.

At determination operation 910, the detected fluctuation in the microcurrent may be evaluated to determine whether it registers below a predetermined threshold. That is, when the detected fluctuation registers below about 12 mA, the specialized screw may imminently traverse and/or fracture the bone. When the detected fluctuation is below about 12 mA, the powered driving device may be automatically shutdown at shutdown operation 914. When the detected fluctuation is not below about 12 mA, the process may continue to determination operation 912.

At determination operation 912, the detected fluctuation in the microcurrent may be evaluated to determine whether the detected fluctuation registers within a predetermined range, e.g., a range between about 12 and 16 mA for example. That is, when the detected fluctuation registers within the predetermined range, the specialized screw may be oriented according to an improper trajectory. When the detected fluctuation is between about 12 and 16 mA, an alert may be generated at alert operation 916. When the detected fluctuation is not between about 12 and 16 mA, the process may return to monitor operation 906.

At shutdown operation 914, the powered driving device may be substantially immediately and automatically shutdown upon a determination that the detected fluctuation registered below the predetermined threshold, as discussed above. According to embodiments, automatic shutdown may be initiated by a safety trigger component. That is, the safety trigger component may be substantially immediately and automatically initiated upon a determination that the detected fluctuation registered below the predetermined threshold, i.e., shutdown may occur substantially instantaneously after determination operation 910.

At alert operation 916, an alert may be generated upon a determination that the detected fluctuation registered within the predetermined range. That is, an alert may be generated such that a clinician may be warned that the specialized screw is oriented according to an improper trajectory, i.e., the specialized screw may not be properly directed toward the target position. According to embodiments, the alert may be generated as an audio alert, a visual alert, or any other suitable alert for communicating a warning to the clinician.

As may be appreciated, description of a method for automatically shutting down a powered driving device during screw placement is provided for purposes of explanation and example only. Indeed, although the method is described as a series of steps, each step should not be understood as a necessary step, as additional and/or alternative steps may be performed within the spirit of the present disclosure. Additionally, described steps may be performed in any suitable order and the order in which steps were described is not intended to limit the method in any way.

Figure 10:
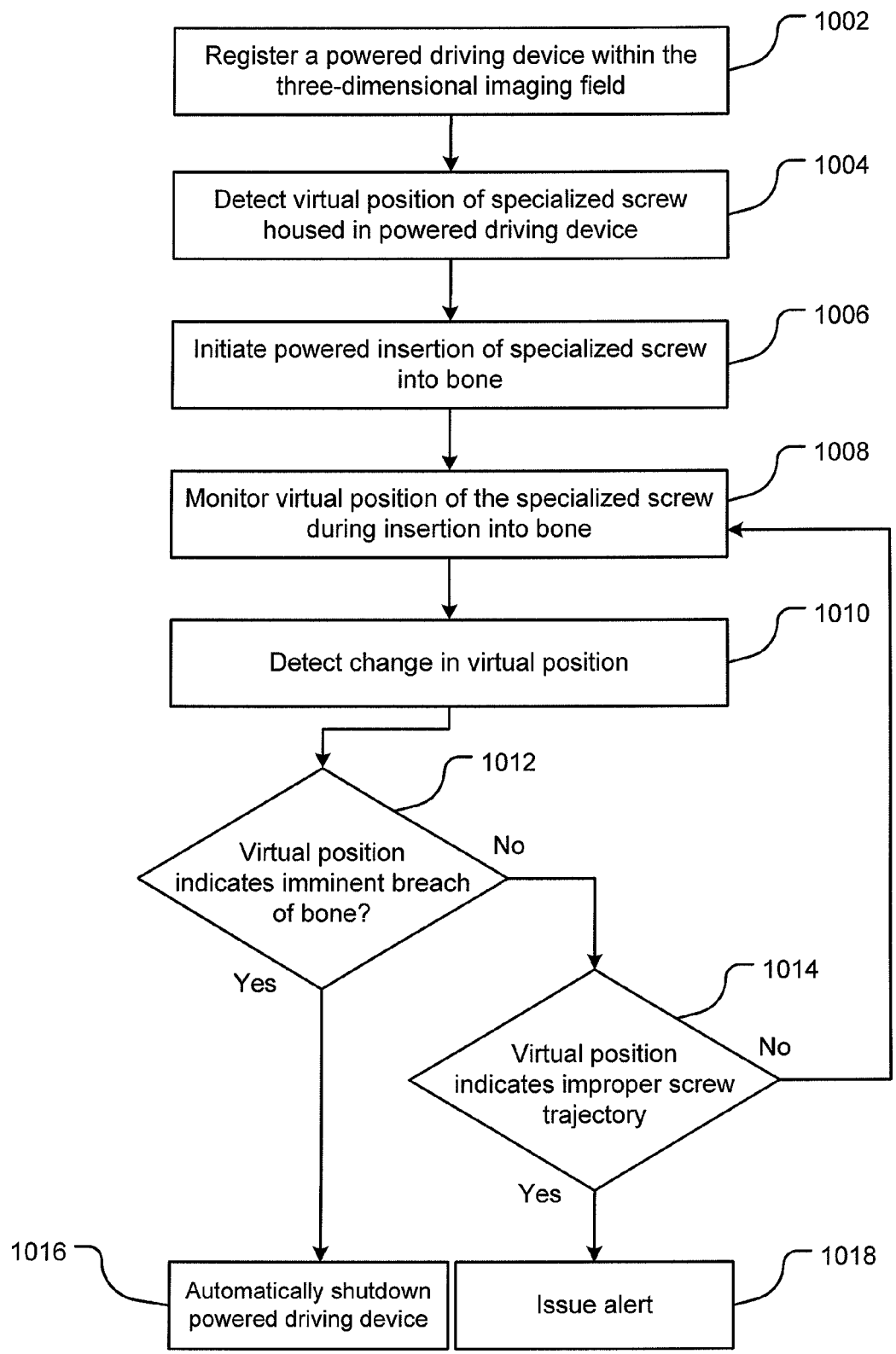
FIG. 10 is a flow-diagram illustrating a second embodiment of a method for automatically shutting down a powered driving device during screw placement.

FIG. 10 is a flow-diagram illustrating a second embodiment of a method for automatically shutting down a powered driving device during screw placement.

At register operation 1002, a powered driving device may be calibrated within an image-guidance field. For example, according to embodiments, the powered driving device may be fitted with light-emitting diodes, global positioning units, magnetic coils, etc., and data regarding the position of the powered driving device may be collected by a stereo camera apparatus, a GPS system, or otherwise. That is, as the detected position of the powered driving device changes within the three-dimensional space of the patient's anatomy, its virtual position on image displays may be simultaneously updated in real time. Further, the exact dimensions of the powered driving device may be loaded into the image-guidance system such that a corresponding virtual powered driving device may be simulated on the display images. According to embodiments, the simulated position and dimensions of the powered driving device may be verified by touching the device to various fiducial markers and/or other known anatomical landmarks and confirming that the simulated position of the powered driving device is within an acceptable degree of deviance, e.g., 1 mm, of the anatomical landmark reflected on each image.

At detect operation 1004, a virtual position of the specialized screw housed in the powered driving device may be determined. That is, according to embodiments, the exact dimensions of the specialized screw may be loaded into the image-guidance system. Thus, as the image-guidance system has knowledge of the registered powered driving device housing the specialized screw, the system may also automatically simulate and project the dimensions of the specialized screw onto each image. Further still, the image-guidance system may identify an orientation of the powered driving device in three-dimensional space, such that a predicted trajectory for the specialized screw may be determined and simulated on the images. Further, upon determining the predicted trajectory, and with knowledge of the exact dimensions of the specialized screw, the image-guidance system may simulate a predicted placement of the specialized screw on the display images.

At initiate operation 1006, after verification of a predicted placement of the specialized screw using the image-guidance system or otherwise, the powered driving device may be initiated, as described above.

At monitor operation 1008, the virtual position of the specialized screw may be monitored in real time. That is, the image-guidance system may continually recalculate and update a virtual position of the specialized screw based on the trajectory of the powered driving device and the exact dimensions of the specialized screw. Additionally or alternatively, according to embodiments, the image-guidance system may be in communication with the powered driving device such that the image-guidance system may be aware of each revolution of the specialized screw as it is being inserted into the bone. That is, as thread dimensions of the specialized screw may be known to the image-guidance system, the system may calculate a depth of the specialized screw associated with each revolution of the specialized screw. According to embodiments, the image-guidance system may then simulate the virtual position of the specialized screw based on a trajectory, length, and depth of the specialized screw in real time for the clinician.

At detect operation 1010, a change in a virtual position of the specialized screw may be detected. Based on the trajectory, length, and depth of the specialized screw, the image-guidance system may determine whether the change in virtual position indicates that the specialized screw is misaligned or otherwise improperly placed. For example, the image-guidance system may compare the virtual position of the specialized screw with a target position communicated by the clinician or otherwise to the image-guidance system.

At determination operation 1012, the detected change in virtual position may be evaluated to determine whether the specialized screw may imminently traverse and/or fracture the bone. That is, by simulating a predicted position of the specialized screw based on the trajectory and length of the specialized screw, for example, the image-guidance system may determine that the specialized screw may imminently breach the cortical bone layer. If so, the powered driving device may be automatically shutdown at shutdown operation 1016. If the detected change in virtual position indicates that the specialized screw should not imminently traverse the bone, the process may continue to determination operation 1014.

At determination operation 1014, the detected change in virtual position may be evaluated to determine whether a virtual trajectory of the specialized screw may be improper. For example, the image-guidance system may compare a virtual trajectory of the specialized screw with a target trajectory calculated by the image-guidance system for delivering the specialized screw into the target position. If the virtual trajectory of the specialized screw is improper, i.e., that the virtual trajectory does not match the target trajectory and may not deliver the specialized screw into the target position, an alert may be generated at alert operation 1018. If the detected change in virtual position indicates that the virtual trajectory of the specialized screw is not improper, the process may return to monitor operation 1008.

At shutdown operation 1016, the powered driving device may be automatically shutdown upon a determination that the detected change in virtual position may imminently traverse the bone. According to embodiments, automatic shutdown may be initiated by a safety trigger component. That is, the safety trigger component may be automatically initiated upon a determination that the detected change in virtual position may imminently traverse the bone, i.e., shutdown may occur substantially instantaneously after determination operation 1012.

At alert operation 1018, an alert may be generated upon a determination that the virtual trajectory of the specialized screw is improper. That is, an alert may be generated such that a clinician may be warned that the virtual trajectory does not match the target trajectory and may not deliver the specialized screw into the target position. According to embodiments, the alert may be generated as an audio alert, a visual alert, or any other suitable alert for communicating a warning to the clinician.

As may be appreciated, description of a method for automatically shutting down a powered driving device during screw placement is provided for purposes of explanation and example only. Indeed, although the method is described as a series of steps, each step should not be understood as a necessary step, as additional and/or alternative steps may be performed within the spirit of the present disclosure. Additionally, described steps may be performed in any suitable order and the order in which steps were described is not intended to limit the method in any way.

Figure 11:
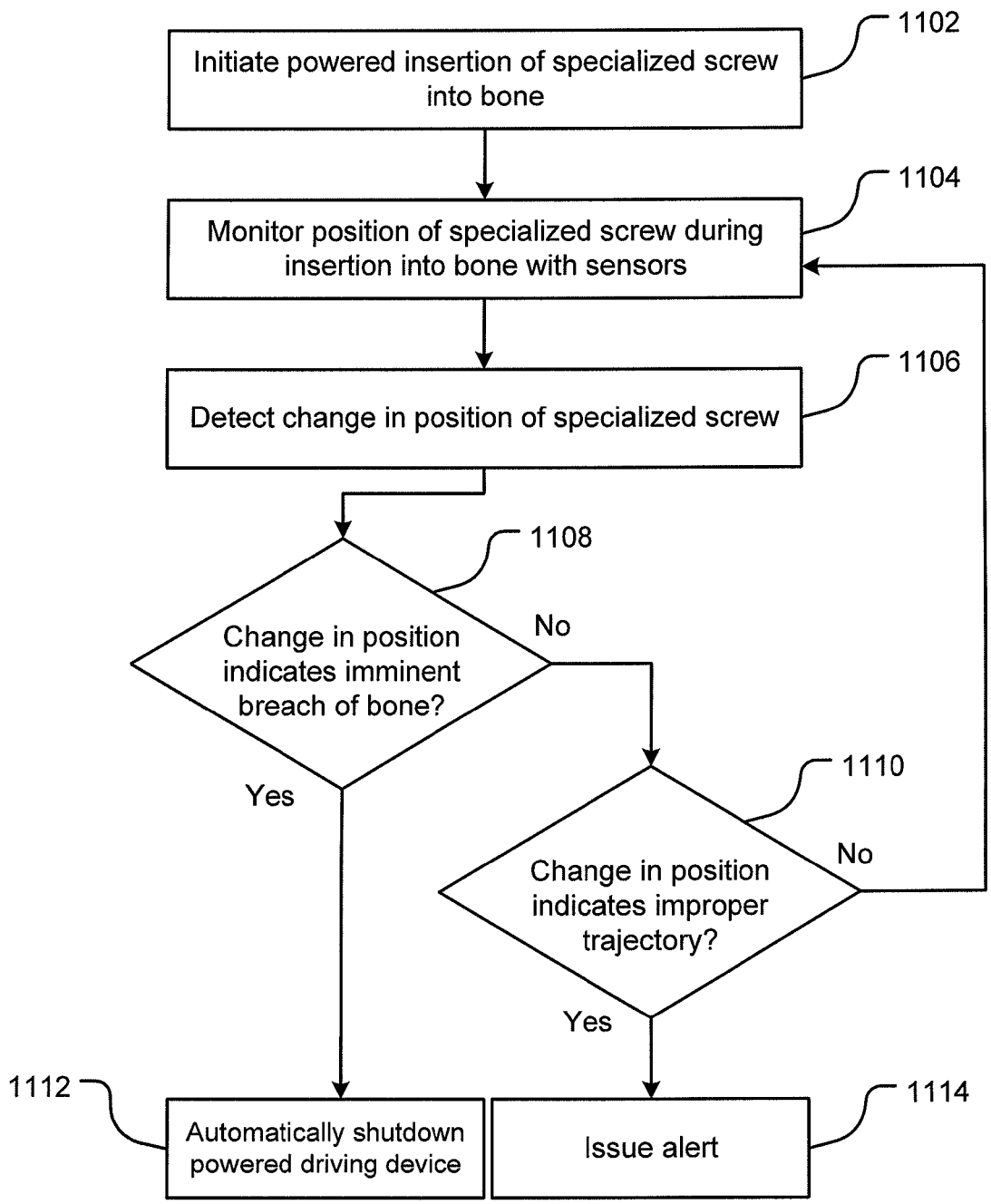
FIG. 11 is a flow-diagram illustrating a third embodiment of a method for automatically shutting down a powered driving device during screw placement.

FIG. 11 is a flow-diagram illustrating a third embodiment of a method for automatically shutting down a powered driving device during screw placement.

At initiate operation 1102, after verification of a projected placement of the specialized screw using the image-guidance system or otherwise, the powered driving device may be initiated, as described above.

At monitor operation 1104, a position of the specialized screw may be monitored by sensors during insertion of the specialized screw. For example, according to embodiments, suitable sensors may be employed to detect a bone density around the specialized screw. As a bone density of the cortical layer may be greater than a bone density of the trabecular layer, bone density may be used to indicate that a specialized screw is approaching the cortical layer and is in danger of traversing and/or fracturing the bone. Alternatively, other suitable sensors may be employed to detect a proximity of the specialized screw to the cortical layer via any other suitable means. For example, sonic devices, radar devices, pressure-sensitive devices, heat-sensitive devices, etc., may be employed to detect bone density and/or a proximity to the cortical layer.

At detect operation 1106, a change in position of the specialized screw may be detected. That is, based on data from the suitable sensors, it may be determined by an associated computing system and/or the powered driving device that the specialized screw is advancing into the bone. Further, the sensors may detect a change in bone density near the specialized screw.

At determination operation 1108, the detected change in position may be evaluated to determine whether the specialized screw may imminently traverse and/or fracture the bone, i.e., the specialized screw is in an improper position. That is, based on data from the suitable sensors, it may be determined by the associated computing system and/or the powered driving device that the specialized screw is in contact with or may imminently traverse the cortical layer. If so, the powered driving device may be automatically shutdown at shutdown operation 1112. If the detected change in position indicates that the specialized screw may not imminently traverse the cortical layer, the process may continue to determination operation 1010.

At determination operation 1010, the detected change in position may indicate that the specialized screw has an improper trajectory. If the trajectory of the specialized screw is improper, i.e., the predicted trajectory does not match the target trajectory and may not deliver the specialized screw into the target position, an alert may be generated at alert operation 1114. If the detected change in position does not indicate an improper trajectory of the specialized screw, the process may return to monitor operation 1104.

At shutdown operation 1112, the powered driving device may be automatically and substantially immediately shutdown upon a determination that the detected change in position may imminently traverse the bone. According to embodiments, automatic shutdown may be initiated by a safety trigger component. That is, the safety trigger component may be automatically initiated upon a determination that the detected change in position may imminently traverse the bone, i.e., shutdown may occur substantially instantaneously after determination operation 1108.

At alert operation 1114, an alert may be generated upon a determination that the trajectory of the specialized screw is improper. That is, an alert may be generated such that a clinician may be warned that specialized screw may not be delivered into the target position based on the improper trajectory. According to embodiments, the alert may be generated as an audio alert, a visual alert, or any other suitable alert for communicating a warning to the clinician.

As may be appreciated, description of a method for automatically shutting down a powered driving device during screw placement is provided for purposes of explanation and example only. Indeed, although the method is described as a series of steps, each step should not be understood as a necessary step, as additional and/or alternative steps may be performed within the spirit of the present disclosure. Additionally, described steps may be performed in any suitable order and the order in which steps were described is not intended to limit the method in any way.

Unless otherwise indicated, all numbers expressing measurements, dimensions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present embodiments. For example, the image-guided placement of any type of screw into any type of bone falls within the scope of the present disclosure. Further, the image-guided placement of screws into the bones of human or non-human vertebrates is well within the scope of the present disclosure. Numerous other changes may be made which will readily suggest themselves to those skilled in the art and which are encompassed in the spirit of the disclosure.

The invention claimed is:

1. A powered driving device for minimal-step placement of a screw into a bone, the powered driving device comprising:
   a drive component configured for delivering torque to a drive shaft, wherein the drive component is powered by a first electrical current;
   the drive shaft communicatively coupled to the drive component, wherein the drive shaft rotates axially when torque is delivered by the drive component;
   a drive chamber that encases the drive component and the drive shaft, the drive chamber for housing a screw, wherein the screw couples to the drive shaft when housed in the drive chamber;
   the screw housed in the drive chamber, wherein the screw is configured to be advanced and inserted into the bone by the axial rotation of the drive shaft, the screw comprising:
      a self-drilling tip, wherein the self-drilling tip is configured to form an impression in an outer cortical region of the bone in the absence of a pre-drilled guide hole;
      a flute, wherein the flute is configured to facilitate advancement of the screw into the bone without fracturing the bone in the absence of pre-tapping; and
      a crown portion at an end of the screw opposite the self-drilling tip;
   a voltage generator for delivering a second electrical current to the screw when the screw is at least partially inserted into the bone;
   a monitoring component for detecting a position of the screw, wherein the monitoring component detects the position of the screw at least in part by measuring the second electrical current to determine a resistance of the bone surrounding the screw;
   an alert component for issuing an alert when the monitoring component detects that the screw has an improper trajectory;

a safety trigger for automatically shutting down the powered driving device when the monitoring component detects the screw is in an improper position; and a stop component for automatically shutting down the powered driving device before the crown of the screw counter-sinks into the bone while the monitoring component detects the screw has a proper trajectory and a proper position, wherein the stop component detects one of: a) a portion of the screw reaching an end of the drive chamber, or b) a portion of the drive shaft reaching an end of the drive chamber.

2. The powered driving device of claim 1, wherein the monitoring component further comprises:
one or more sensors for detecting the position of the screw as the screw is delivered into bone.

3. The powered driving device of claim 1, wherein the bone is a vertebral bone.

4. The powered driving device of claim 1, wherein the monitoring component further comprises:
a meter for monitoring the second electrical current flowing through the screw and into the bone, wherein the second electrical current registers below a predetermined threshold when the screw is in an improper position, and wherein the second electrical current registers within a predetermined range when the screw has an improper trajectory.

5. The powered driving device of claim 1, wherein the monitoring component further comprises:
one or more sensors for detecting the position of the screw.

6. The powered driving device of claim 1, wherein the monitoring component further comprises:
an image-guidance tracker affixed to the powered driving device; and
an image-guidance system for calculating a predicted position of the screw based on data from the image-guidance tracker.

7. A powered driving device for minimal-step placement of a screw into a bone, the powered driving device comprising:
a drive component configured for delivering torque to a drive shaft, wherein the drive component is powered by a first electrical current;
the drive shaft communicatively coupled to the drive component, wherein the drive shaft rotates axially when torque is delivered by the drive component;
a drive chamber that encases the drive component and the drive shaft, the drive chamber for housing a screw, wherein the screw couples to the drive shaft when housed in the drive chamber;
the screw housed in the drive chamber, wherein the screw is configured to be advanced and inserted into the bone by the axial rotation of the drive shaft, the screw comprising:
a self-drilling tip, wherein the self-drilling tip is configured to form an impression in an outer cortical region of the bone in the absence of a pre-drilled guide hole;
a flute, wherein the flute is configured to facilitate advancement of the screw into the bone without fracturing the bone in the absence of pre-tapping; and
a crown portion at an end of the screw opposite the self-drilling tip;
a voltage generator for delivering a second electrical current to the screw when the screw is at least partially inserted into the bone;
a meter for measuring the second electrical current flowing through the screw and into the bone;
a monitoring component for detecting a position of the screw, wherein the monitoring component is communicatively coupled to the meter, wherein the monitoring component detects the position of the screw based at least in part on estimating a resistance of the bone surrounding the screw;
a safety trigger for automatically shutting down the powered driving device when the monitoring component detects the screw is in an improper position; and
a stop component for automatically shutting down the powered driving device before the crown of the screw counter-sinks into the bone while the monitoring component detects the screw has a proper position, wherein the stop component detects one of: a) a portion of the screw reaching an end of the drive chamber, or b) a portion of the drive shaft reaching an end of the drive chamber.

8. The powered driving device of claim 7, wherein the monitoring component further comprises:
one or more sensors for detecting the position of the screw as the screw is delivered into bone.

9. The powered driving device of claim 7, further comprising an alert component for issuing an alert when the monitoring component detects that the screw has an improper trajectory.

10. The powered driving device of claim 7, wherein the second electrical current registers below a predetermined threshold when the screw is in an improper position, and wherein the second electrical current registers within a predetermined range when the screw has an improper trajectory.

11. The powered driving device of claim 7, wherein the monitoring component further comprises:
one or more sensors for detecting the position of the screw.

12. The powered driving device of claim 7, wherein the monitoring component further comprises:
an image-guidance tracker affixed to the powered driving device; and
an image-guidance system for calculating a predicted position of the screw based on data from the image-guidance tracker.

13. A powered driving device for minimal-step placement of a screw into a bone, the powered driving device comprising:
a drive component configured for delivering torque to a drive shaft, wherein the drive component is powered by a first electrical current;
the drive shaft communicatively coupled to the drive component, wherein the drive shaft rotates axially when torque is delivered by the drive component;
a drive chamber that encases the drive component and the drive shaft, the drive chamber for housing a screw, wherein the screw couples to the drive shaft when housed in the drive chamber;
the screw housed in the drive chamber, wherein the screw is configured to be advanced and inserted into the bone by the axial rotation of the drive shaft, the screw comprising:
a self-drilling tip, wherein the self-drilling tip is configured to form an impression in an outer cortical region of the bone in the absence of a pre-drilled guide hole;
a flute, wherein the flute is configured to facilitate advancement of the screw into the bone without fracturing the bone in the absence of pre-tapping; and
a crown portion at an end of the screw opposite the self-drilling tip;
a voltage generator for delivering a second electrical current to the screw when the screw is at least partially inserted into the bone;

a meter for measuring the second electrical current flowing through the screw and into the bone;

a monitoring component for detecting a position of the screw, wherein the monitoring component is communicatively coupled to the meter, wherein the monitoring component detects the position of the screw based at least in part on estimating a resistance of the bone surrounding the screw;

an alert component for issuing an alert when the monitoring component detects that the screw has an improper trajectory; and a stop component for automatically shutting down the powered driving device before the crown of the screw counter-sinks into the bone while the monitoring component detects the screw has a proper trajectory, wherein the stop component detects one of: a) a portion of the screw reaching an end of the drive chamber, or b) a portion of the drive shaft reaching an end of the drive chamber.

14. The powered driving device of claim 13, further comprising a safety trigger for automatically shutting down the powered driving device when the monitoring component detects the screw is in an improper position.

15. The powered driving device of claim 13, wherein the second electrical current registers below a predetermined threshold when the screw is in an improper position, and wherein the second electrical current registers within a predetermined range when the screw has an improper trajectory.

16. The powered driving device of claim 13, wherein the monitoring component further comprises:

an image-guidance tracker affixed to the powered driving device; and an image-guidance system for calculating a predicted position of the screw based on data from the image-guidance tracker.

* * * * *